(12) United States Patent
Vogt et al.

(10) Patent No.: US 11,751,899 B2
(45) Date of Patent: Sep. 12, 2023

(54) DIFFERENTIAL PRESSURE MOTOR AND METHOD FOR OPERATING A DIFFERENTIAL PRESSURE MOTOR

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 580 days.

(21) Appl. No.: 15/931,170

(22) Filed: May 13, 2020

(65) Prior Publication Data

US 2020/0367922 A1  Nov. 26, 2020

(30) Foreign Application Priority Data

May 22, 2019  (DE) .......................... 102019113640.7

(51) Int. Cl.
*A61B 17/3203* (2006.01)
*A61B 17/14* (2006.01)
(Continued)

(52) U.S. Cl.
CPC .......... *A61B 17/3203* (2013.01); *A61B 17/14* (2013.01); *A61B 17/1628* (2013.01);
(Continued)

(58) Field of Classification Search
CPC ......... F15B 11/076; F15B 11/15; F15B 11/06; F15B 2211/7725; F15B 2211/8855;
(Continued)

(56) References Cited

U.S. PATENT DOCUMENTS 3,625,246 A * 12/1971 Reaves .................. F16K 31/128
  137/488
3,682,198 A *  8/1972 Davis .................. F16K 31/5286
  137/625.25
(Continued)

FOREIGN PATENT DOCUMENTS

DE   2654629 A1   6/1978
DE   3508726 A1   9/1986
(Continued)

*Primary Examiner* — Matthew J Lawson
(74) *Attorney, Agent, or Firm* — Dicke, Billig & Czaja, PLLC

(57) ABSTRACT

A differential pressure motor comprising two working pistons and a rod that move in a hollow space. Walls defining the hollow space have five openings. A valve piston moves between and against the working pistons and can be driven by the working pistons. The valve piston with the five openings forms a valve with which an alternate impact of a first pressure and a second pressure on the working pistons is controllable when the pressures are applied to three of the five openings such that the working pistons periodically move which drives a periodic movement of the valve piston. Also disclosed are a surgical drive system with, a medical lavage system for the debridement of soft tissue and/or bone tissue having, and a medical device for brushing, rasping or sawing soft tissue and/or bone tissue with such a differential pressure motor, and a method for operating a differential pressure motor.

32 Claims, 11 Drawing Sheets

(51) Int. Cl.
*A61B 17/16* (2006.01)
*F04B 9/131* (2006.01)
*F15B 15/14* (2006.01)
*A61B 17/00* (2006.01)

(52) U.S. Cl.
CPC .......... *A61B 17/1659* (2013.01); *F04B 9/131* (2013.01); *F15B 15/149* (2013.01); *F15B 15/1414* (2013.01); *A61B 2017/00398* (2013.01); *A61B 2017/32035* (2013.01)

(58) Field of Classification Search
CPC ........ F16K 11/07; F16K 11/065; F16K 11/06; A61B 17/16; A61B 17/1624; A61B 17/1628; A61B 17/1657; A61B 17/17; A61B 17/142; G05D 16/0404; F04B 9/00; B27B 19/00; B27B 19/002; B27B 19/004; B27B 19/006; B27B 19/02; B27B 19/04; B27B 19/06; B27B 19/065; B27B 19/09
See application file for complete search history.

(56) References Cited

U.S. PATENT DOCUMENTS

| | | | | |
|---|---|---|---|---|
| 4,036,106 A | * | 7/1977 | Athy, Jr. | F15B 11/08 60/403 |
| 4,278,078 A | | 7/1981 | Smith | |
| 4,583,531 A | | 4/1986 | Mattchen | |
| 4,606,257 A | * | 8/1986 | Pfister | F15B 11/06 91/32 |
| 4,700,612 A | * | 10/1987 | Pfister | F15B 11/06 91/27 |
| 4,722,262 A | * | 2/1988 | Schneider | F15B 11/15 91/468 |
| 4,993,924 A | | 2/1991 | Mukumoto et al. | |
| 5,065,665 A | * | 11/1991 | Kimura | F15B 11/06 91/461 |
| 5,184,535 A | * | 2/1993 | Kimura | F15B 11/05 91/448 |
| 5,184,643 A | * | 2/1993 | Raymond | F16K 11/07 137/625.48 |
| 5,261,314 A | * | 11/1993 | Kimura | F15B 11/06 91/461 |
| 5,485,887 A | * | 1/1996 | Mandanis | B25D 17/06 173/91 |
| 5,542,918 A | | 8/1996 | Atkinson | |
| 5,554,011 A | | 9/1996 | Bales et al. | |
| 5,887,665 A | * | 3/1999 | Seifert | B25D 9/14 173/206 |
| 6,272,968 B1 | * | 8/2001 | Ropponen | F15B 11/15 91/308 |
| 6,276,257 B1 | * | 8/2001 | Hellemann | F15B 13/0405 91/442 |
| 6,336,925 B1 | | 1/2002 | Malak | |
| 8,292,909 B1 | | 10/2012 | DuBois et al. | |
| 9,546,737 B1 | * | 1/2017 | Wang | F16K 31/426 |
| 9,593,578 B2 | | 3/2017 | Vogt et al. | |
| 9,861,770 B2 | | 1/2018 | Vogt | |
| 11,359,650 B2 | * | 6/2022 | Tadje | F15B 13/0402 |
| 2005/0084395 A1 | | 4/2005 | Kang | |
| 2007/0075286 A1 | * | 4/2007 | Tanner | F16K 11/07 251/129.06 |
| 2007/0233131 A1 | * | 10/2007 | Song | A61B 17/1671 606/79 |
| 2015/0141904 A1 | | 5/2015 | Vogt | |
| 2015/0308421 A1 | | 10/2015 | Vogt | |
| 2020/0025224 A1 | * | 1/2020 | Takakuwa | F15B 11/064 |
| 2021/0040946 A1 | * | 2/2021 | Heitmann | F15B 11/024 |
| 2021/0291215 A1 | * | 9/2021 | Doi | B05B 1/005 |

FOREIGN PATENT DOCUMENTS

| | | |
|---|---|---|
| DE | 3514787 A1 | 10/1986 |
| DE | 3724110 A1 | 2/1989 |
| DE | 69800998 T2 | 4/2002 |
| DE | 102014208064 B4 | 12/2015 |
| EP | 2873856 | 5/2015 |
| EP | 2910270 | 8/2017 |
| WO | 2012/038003 | 3/2012 |

* cited by examiner

DIFFERENTIAL PRESSURE MOTOR AND METHOD FOR OPERATING A DIFFERENTIAL PRESSURE MOTOR

CROSS-REFERENCE TO RELATED APPLICATIONS

This application claims priority under 35 U.S.C. § 119(a) to German (DE) Patent Application No. 10 2019 113 640.7, filed on May 22, 2019.

TECHNICAL FIELD

The invention relates to a differential pressure motor, a surgical drive system with such a differential pressure motor, a medical lavage system for the debridement of soft tissue and/or bone tissue having such a differential pressure motor and a medical device for brushing, rasping or sawing soft tissue and/or bone tissue with such a differential pressure motor, and a method for operating a differential pressure motor. The differential pressure motor is suitable for driving medical devices for lavaging and debriding soft and bone tissue. The medical devices driven by the differential pressure motor are preferably designed for single use for reasons of hygiene.

BACKGROUND OF THE DISCLOSURE

Unfortunately, in orthopedic surgery, it is necessary, to a certain degree, to make septic revisions of joint prostheses that have been infected with microorganisms. The infected joint prostheses are taken out and the infected or necrotic tissue is removed. This removal of infected/necrotic tissue is known as debridement. Debridement can be conducted by rinsing the wound using so-called lavage systems, and by cutting out, rasping, sawing and brushing. The devices used for debridement are contaminated with tissue residue and microbial germs following debridement. These instruments must be carefully cleaned and then sterilized before being used again. The medical staff must protect themselves against contamination or infection by the transfer of microbial germs during cleaning work. It is therefore desirable if a low-cost device with a motor drive could be made available for rasping, sawing and brushing for septic revisions, which could be discarded with the usual operating procedure (OP) waste after single use, without extensive cleaning steps that themselves are a potential hazard. In order to conserve resources and protect the environment, as well as for cost reasons, it would be advantageous if the drive did not require batteries, rechargeable batteries and electric motors.

Currently, drive devices are known in the medical field that are driven with compressed air and electrical energy. Most of the drive systems that are based on compressed air contain lamella motors. One problem is that unsterile compressed air is supplied through a hose and after the motor has been driven, the expanded, unsterile air must be discharged out of the operating theater via a separate hose. In many cases, coaxial hose systems are used for this purpose. The drives driven with compressed air have been largely replaced by electrically driven drive systems. These drive systems contain electric motors with gear units and usually use rechargeable batteries as a source of energy. The electrically driven drive systems contain copper and other heavy metals.

In lavage systems, spray jets are generated from rinsing fluids, which impact on the areas of tissue to be cleaned and exert a mechanical cleaning effect on these areas of tissue. Pulsed lavage systems have been known for a long time, for example from U.S. Pat. Nos. 4,583,531, 4,278,078 and 5,542,918.

However, when compressed air-driven lavage systems are used, a double hose system is required, in which the unsterile compressed air is supplied in one hose, while in a second hose, unsterile air is discharged that is at least partially expanded following the drive of the compressed air motor. In systems driven by compressed air or another compressed gas, a compressed gas motor is usually used as a drive. A compressed gas motor of this type is known from International Patent Application Publication No. WO 2012/038003 A1. The compressed gas motor described there has a dual-part piston with an interim space and a passage through one of the piston parts. As a result, the structure of the motor is particularly simple and low-cost. A compressed gas motor for a spray can is known from German Patent Document No. DE 37 24 110 A1. A reciprocating pump driven with compressed gas is known from U.S. Pat. No. 4,993,924. A compressed gas motor for a lavage system is known from European Patent Document No. EP 2 873 856 A1. In this compressed gas motor, a control piston is moved by a working piston via a carrier element, and as a result, during operation of the compressed gas motor, a gas inlet opening and a gas outlet opening are periodically opened and closed.

In a large number of operations, it is necessary to suction out wound secretion and blood. In order to suction out these liquids, suction devices are used that are operated with an underpressure. In order to operate these devices, in most operating theaters stationary vacuum systems are provided that usually provide an underpressure of 0.8 bar to 0.9 bar. In addition, mobile vacuum suction systems, or suction systems that generate an underpressure, are widely used.

There is always a desire for a motor that can be constructed at low cost. In addition, there is also a need to provide a motor that can be operated with a higher frequency and/or a greater force.

U.S. Pat. No. 5,554,011 discloses a pump with a differential pressure motor in which a valve element is controlled by the movement of a membrane. On the membrane, the work is performed by the changing gas pressure and as a result, the pump is driven. The construction of this differential pressure motor is relatively complex and due to the membrane and the necessary tension of the membrane, different vibration behavior may occur for differential pressure motors with the same structure. In addition, with the valve element, there is a risk of a dead point, from which the differential pressure motor can no longer continue to run of its own accord.

With U.S. Pat. No. 9,861,770, a vacuum motor is proposed in which a spiral spring is tensioned through the impact of a vacuum on a piston. At the end of the tensioning procedure, an impulse is delivered onto a valve piston, which opens ventilation openings and closes the vacuum openings for a brief period. The tensioned spiral spring can expand and drives the piston back into the initial position, and thus drives a connected pump piston. A periodic, linear, oscillating pump movement is generated that is driven by the spiral spring, wherein the spiral spring is tensioned by a pressure difference.

A liquid pump for a lavage system is known from U.S. Pat. No. 5,542,918, which is driven by an underpressure and in which a membrane is driven by a hollow, linearly movable and elastically supported piston, in which a valve piston, which is also elastically supported, is disposed for opening and closing a gas inlet for feeding air. The system has the disadvantage that the valve element, when opened, can only provide a small free flow profile. As a result, the force generated by the pump is limited and there is the risk of a dead point from which the pump cannot re-start of its own accord. In addition, due to the lack of guidance of the valve piston, side movements of the valve piston may occur, and this may lead to irregular oscillations of the piston.

U.S. Patent Application Publication No. 2005/0084395 discloses a vacuum-driven lavage system that operates via two cylinders. In the cylinders, two pistons that are coupled to each other are driven by the vacuum.

In European Patent No. EP 2 910 270 B1 and U.S. Pat. No. 9,861,770, a differential pressure motor is described for driving a pump for a lavage system. The differential pressure motor consists of an axially movable working piston in a hollow space and a return element disposed behind it. The working piston has a carrier element that moves a control piston when in operation. The control piston is a hollow cylinder and can cover a gas outlet opening and a gas inlet opening with its closed sheath surface. An underpressure source such as a vacuum pump is connected to the gas outlet opening. This means that the gas outlet opening and the gas inlet opening are periodically covered during operation of the motor. When the gas outlet opening is opened, the air is suctioned out from the differential pressure motor, while the working piston is moved against the return element. At the same time, the feed air opening is closed by the control piston. The return element is tensioned. Then, the carrier element issues an impulse to the control piston. The control piston moves away from the working piston and opens the gas inlet opening, while at the same time closing the gas outlet opening. The vacuum collapses and the return element moves the working piston into its initial position. Then, the carrier sends an impulse to the control piston. The control piston moves in the direction of the working piston. The gas inlet opening is closed by the sheath surface of the control piston and the gas outlet opening is opened. Then the cycle starts again. This differential pressure motor is designed for high pulse rates of approximately 2,000 pulses per minute for operating a pump for a lavage system. The stroke length is relatively short and is between 2 and 5 mm. For brushing, rasping or sawing, larger stroke lengths and lower pulse rates are required. For the production of the differential pressure motor described in European Patent No. EP 2 910 270 B1 and U.S. Pat. No. 9,861,770, components made by synthetic material precision injection molding are required. A great deal of care is needed when mounting these components.

The forces achievable with the vacuum motors are entirely sufficient for spraying liquids. However, larger drive forces are required for driving saws, rasps and brushes.

In U.S. Pat. No. 8,292,909, a double-acting vacuum motor is described. In this motor, a force is transferred onto a valve piston by a bi-stable coupling element at the end of the forward and backward movement of the working piston, as a result of which the valve piston moves from one switching state into a second switching state. As a result, the valve piston remains in a defined switching state during the movement of the working piston. Thus, due to the respective end position of the working piston, the switching state of the valve piston is defined.

An object of the present invention therefore consists in overcoming the disadvantages of the prior art. In particular, an object of the invention consists in developing a differential pressure motor that is low-cost and easy to produce, that works reliably, is variable in its use and that with the aid of a pressure difference, in particular an underpressure source or a compressed gas source, such as those available in hospitals, achieves sufficient power to debride tissue and/or to drive tools used for surgery. It is therefore also an object of the present invention to provide such surgical tools and lavage systems with such a differential pressure motor. Equally, it is an object of the present invention to provide a method for operating a differential pressure motor, wherein the method offers the advantages described above in relation to the differential pressure motor.

It is also an object of the invention to develop an extremely simplified, low-cost differential pressure motor that can be driven with a vacuum or underpressure or with compressed gas or also with a pressurized liquid, and that generates an oscillating, linear movement. The differential pressure motor should be simpler to construct and cheaper to produce than known differential pressure motors for driving a lavage system. The differential pressure motor should as far as possible be designed such that the vacuum provided via central vacuum systems in operating theaters is sufficient for its operation. The stroke of the differential pressure motor should preferably be greater than 5 mm, in order to be able to operate tools such as brushes or saws in the medical field effectively and without additional gear units. The differential pressure motor should be suitable for driving lavage systems and devices used for debriding infected soft and bone tissue, which for reasons of hygiene are only designed for single use as so-called disposable devices. The differential pressure motor should be sterilizable with ethylene oxide.

It is also an object of the invention to develop a differential pressure motor that is suitable as a drive to be used once for medical saws, rasps, brushes and rinsing devices. As far as possible, no mechanical springs should be used for the drive. It should essentially be possible to form the differential pressure motor from synthetic materials. As a result, it should be possible to dispose of the differential pressure motor through combustion following its use. Further, the intention is to develop a medical drive unit with the vacuum motor. This drive unit is to be suitable for driving medical saws, rasps, brushes and rinsing devices. This drive unit is in particular designed for septic revisions in orthopedics, which are caused by infections with problematic microbial germs, such as MRSA (methicillin-resistant *Staphylococcus aureus*) and VRSA (vancomycin-resistant *Staphylococcus aureus*). Conventional electrically driven drive units must be thoroughly cleaned, disinfected and sterilized after the OP. This work is cost-intensive and entails a not inconsiderable risk of infection for medical staff. The differential pressure motor to be developed and the drive units constructed with the differential pressure motor are therefore designed for single use and should be hygienically disposable through combustion together with other hospital waste. For this reason, the differential pressure motor and the entire medical drive unit should essentially consist of low-cost synthetic material parts, which can be produced using synthetic material injection molding and can be disposed of hygienically and at low cost through combustion. The drive unit and the differential pressure motor should further be designed such that any microbial contamination of the stationary vacuum systems is excluded.

SUMMARY OF THE DISCLOSURE

The objects that form the basis of the present invention are attained by a differential pressure motor comprising two working pistons each with a working surface, a rod that connects the working pistons to each other and keeps them spaced apart from each other, a hollow space that is at least partially cylindrical, wherein the working pistons and the rod are movably disposed in the hollow space, wherein five complete openings are disposed in walls of the hollow space, a valve piston, wherein the valve piston is movably disposed between the working pistons against the working pistons and the valve piston is able to be driven through thrusts of the working pistons against the valve piston and is movable in the cylindrical hollow space, wherein the valve piston with the five complete openings forms a valve with which an alternate impact of a first pressure and a second pressure on the working surfaces of the working pistons is controllable when the first pressure and the second pressure are applied to three of the five complete openings such that a periodic movement of the working pistons and the rod is created in the hollow cylinder, which drives a periodic movement of the valve piston.

The two working pistons and the rod are movably disposed in the hollow space against the hollow space.

Preferably, the valve piston is able to be driven on both sides by impacts of the working piston against the valve piston.

As used in this document, a working surface of a working piston is regarded as being the side of the working piston on which the work on the working piston is performed due to changing pressure conditions, i.e., due to the alternate impact of the first pressure and the second pressure.

The first pressure and the second pressure are preferably conveyed via a fluidic working medium. For this purpose, the ambient air pressure surrounding the differential pressure motor and a vacuum or an underpressure can preferably be used.

Alternatively, however, a compressed gas and the surrounding ambient air pressure, a vacuum or an underpressure and a compressed gas, and theoretically also a pressurized liquid opposite a free outlet for the liquid can be used as a fluidic working medium for providing the first pressure and the second pressure. A compressed gas can for example be generated with a compressor or by the evaporation of $CO_2$ from a $CO_2$ compressed gas canister. Further, water vapor can also be generated by the evaporation of water through the impact of heat, in order to generate a pressurized water vapor as the fluidic working medium. The differential pressure motor can therefore also be used as a steam-driven motor. However, the use of the differential pressure motor as a vacuum motor is preferred, particularly for medical applications, since connections for this are usually available in operating theaters.

Preferably, the five openings are disposed adjacent to each other in an axial relation to a cylinder axis of the hollow space, particularly preferably along a row. Then, the five openings are axially adjacent to each other in a row, so that the five openings are formed by a central opening, two outer openings and two openings adjacent to the outer openings, wherein the two openings adjacent to the outer openings are disposed between one of the outer openings respectively and the central opening. The cylinder axis of the hollow space is particularly preferably the cylinder axis of a valve space in which the valve piston is movably disposed.

The central opening, outer openings and openings adjacent to the outer openings relate to the place at which the openings open out into the hollow space or the valve space. However, this arrangement preferably also corresponds to the arrangement of the complete openings that open outward from the wall of the hollow space. The complete openings can then simply run straight through the wall along the shortest route.

A cylinder or a cylindrical geometry in the sense of the present invention is, as is also the case with the general definition, a body bounded by two parallel, planar, congruent surfaces (base and cover surface) and a sheath surface or cylinder surface, wherein the sheath surface is formed by parallel straight lines. This means that the cylinder is created by displacing a planar surface along a straight line that is not on this plane. The height and the axis of the cylinder are provided by the distance between the two planes on which the base and cover surface lie.

If the straight lines are vertical to the base and cover surface, the cylinder is known as a straight cylinder. The straight cylindrical geometry of the interior space is preferred according to the invention. In the sense of the present invention, a straight circular cylinder is therefore only a specific case of a cylindrical geometry, but is also preferred due to the simpler production involved.

In this document, an axial direction is regarded as being the direction in relation to the cylinder axis of the at least partially cylindrical hollow space.

Preferably, the valve piston is a rotationally symmetric body that is movably disposed along its symmetry axis in the hollow space.

Preferably, the hollow space is bounded by two closed front surfaces. The rod protrudes from the hollow space through one or more recesses in the front surface or the front surfaces. For this purpose, the rod can be guided through one of the working pistons or through both working pistons.

Preferably, the differential pressure motor is designed for single use. For this purpose, the differential pressure motor can essentially consist of flammable synthetic material.

The hollow space is cylindrical, at least in the area of the displacement of the two working pistons and in a valve space over which the valve piston can travel.

The hollow space has two cylindrical working spaces, in which the two working pistons are movably disposed.

The differential pressure motor is drivable using compressed gas and/or a vacuum.

If the differential pressure motor can be driven with a vacuum or an underpressure, it can be termed a vacuum motor. If the differential pressure motor can be driven with a compressed gas or an overpressure, it can be termed a compressed gas motor.

According to the present invention, the working pistons divide the hollow space into at least three areas that are separated from each other.

As a result, efficient operation and a high power of the differential pressure motor are made possible.

Additionally, the hollow space has a first working space and a second working space in which the working pistons are movably disposed, and has a valve space disposed between the working spaces, wherein the five complete openings are disposed in the valve space in each position of the working pistons.

Thus, a movement of the valve piston in the valve space is made possible, wherein in the valve space, the movement of the valve piston is not impaired by alternating pressure conditions or the performance of work.

Preferably, the first working space and the second working space have a larger profile than the valve space.

The valve space is preferably bounded by the sides of the working piston opposite the working surfaces and an inner wall that is at least partially cylindrical and bounds the hollow space in certain areas.

The valve piston is then disposed in the valve space, preferably on the rod and movably disposed against the rod.

Each of the working spaces can then be connected in a gas-permeable manner to one of the five openings, so that the pressure in the working spaces can be controlled by the valve.

Preferably, all free areas of the valve space are connected to each other in a gas-permeable manner. Thus, a situation is prevented in which the movement of the valve piston is impeded by a build-up of gas cushions in the valve space. For this purpose, two front sides of the valve piston are connected to each other in a gas-permeable manner in the hollow space.

According to a preferred further development of the present invention, the axial distance between a first front surface of the valve piston and the rear side of the adjacent working piston is smaller than or equal to the distance between the working surface of this working piston and a first front surface of the hollow space, and the axial distance between a second front surface of the valve piston and the rear side of the adjacent working piston is smaller than or equal to the distance between the working surface of this working piston and a second front surface of the hollow space that is located opposite the first front surface.

It is thus ensured that the stroke movement of the working pistons is sufficient to reach the valve piston and as a result to impact it and thus to drive the valve.

The working pistons and the rod are disposed linearly movably, in particular axially movably, in relation to a symmetry axis of the working pistons and/or the rod, in the at least partially cylindrical hollow space.

As a result, a periodic linear movement is generated that can be directly used for medical purposes such as sawing, rasping, brushing or pumping.

Preferably, the valve piston with the five openings forms a 2/5-way valve, preferably a 2/5-way impulse valve.

A 2/5-way valve is also known as a 2-position 5-way valve. Such 2/5-way valves are particularly well suited for the differential pressure motor according to the invention and enable a stable and reliable control of the pressure conditions in the differential pressure motor.

Additionally, the valve controls an alternate impact of a vacuum or a compressed gas and of the surrounding atmosphere on the working piston.

Thus, with the aid of the valve, a periodic movement of the differential pressure motor is generated.

Preferred differential pressure motors according to the invention can also be characterized by the fact that the working surfaces of the working pistons are aligned facing away from each other.

As a result, the space in which the valve piston moves can be spatially separated from the working spaces in which the work on the working pistons is performed, so that a direct influence of the pressure conditions in the working spaces on the movement of the valve piston can be excluded.

Preferably, it can further be provided that the valve piston is disposed on the rod in an axially displaceable manner.

As a result, the support of the valve piston and thus the movement of the valve piston is stabilized.

According to a preferred further development of the present invention, the valve piston is a sheath with three circumferential grooves, which are separated from each other by circumferential bridges, wherein the grooves are at least as broad as the axial distance of two axially adjacent openings of the five openings relative to the sheath, so that with a suitable position of the sheath in the hollow space, two axially adjacent openings open out into the same groove of the sheath in the hollow space, and wherein preferably, the bridges are as broad, at least in the axial direction, as the apertures into the hollow space of both openings of the five openings which are adjacent to the outermost openings.

Thus, it is ensured that the valve piston is suitable for controlling the valve in every position.

Further, a central opening of the five openings is connected to a vacuum port or a compressed air port and two outer openings are open outward to the area surrounding the differential pressure motor, or two outer openings of the five openings are connected to a vacuum port or a compressed air port and a central opening is open outward to the area surrounding the differential pressure motor.

As a result, the differential pressure motor is suitable for use with an underpressure or a vacuum or for use with an overpressure or a compressed gas. The normal pressure or ambient pressure surrounding the differential pressure motor is always used as a second pressure.

For the same purpose, a central opening of the five openings is connected to a vacuum port or a compressed air port, or two outer openings of the five openings are connected to a vacuum port or a compressed air port.

Further, an opening that is adjacent to an outer opening of the five openings is connected to a first working space that is bounded by a first working piston of the two working pistons in a pressure-conductive manner, and another opening that is adjacent to an outer opening is connected to a second working space that is bounded by a second working piston of the two working pistons in a pressure-conductive manner.

Thus, the adjacent openings of the five openings can be connected to each other via a single broad groove in the surface of the valve piston and the valve can thus control the pressure conditions in a simple manner.

Further, when a vacuum is applied to a vacuum port of the differential pressure motor provided for this purpose, the two working pistons create an oscillating movement of the rod through the periodic change between the effect of the vacuum and the surrounding atmosphere, or when a compressed gas is introduced at a compressed gas port of the differential pressure motor provided for this purpose, the two working pistons create an oscillating movement of the rod through the periodic change between the effect of the compressed air and the surrounding atmosphere, wherein in both cases, the working pistons periodically impact the valve piston on both sides, thus creating an axial periodic movement of the valve piston, as a result of which the valve is switched.

As a result, a simple and secure control of the differential pressure motor is achieved.

According to a further development of the present invention, in a first position of the valve piston a first central opening of the five openings and a second opening of the five openings that is adjacent to the first opening are connected in a gas-conductive manner via the valve, and a third opening of the five openings that is located opposite the second opening relative to the first opening and a fourth opening of the five openings adjacent to it on the edge side are connected to each other in a gas-conductive manner, and the five openings are otherwise separated from each other in a gas-tight manner in the hollow space by the valve, and in a second position of the valve piston, the first central opening and the third opening are connected to each other in a gas-conductive manner via the valve, and the second opening and a fifth opening of the five openings adjacent to it on the edge side are connected to each other in a gas-conductive manner, and the five openings are otherwise separated from each other in a gas-tight manner in the hollow space by the valve.

Thus, a simple 2/5-way valve control is realized, which enables a reliable control of the differential pressure motor.

The valve piston is transferable from the first position of the valve piston to the second position of the valve piston by an impulse transmission of a first working piston of the two working pistons onto the valve piston, and the valve piston is transferable from the second position of the valve piston to the first position of the valve piston by an impulse transmission of a second working piston of the two working pistons onto the valve piston.

Thus, the valve piston can be driven by the working pistons in a simple manner.

Further, the first working piston in the first position of the valve piston is accelerated in the direction of the valve piston due to a pressure bearing on the working surface of the first working piston, and the second working piston in the second position of the valve piston is accelerated in the direction of the valve piston due to a pressure bearing on the working surface of the second working piston.

As a result, the working pistons achieve the necessary momentum to transmit an impulse onto the valve piston. Thus, due to its inertia, the valve piston can easily be transferred into both positions without the valve piston coming to a halt at a dead point position during the operation of the differential pressure motor.

Further, a first working space, which is bounded by the first working piston, is connected to the second opening in a gas-conductive manner, and a second working space, which is bounded by the second working piston, is connected to the third opening in a gas-conductive manner.

As a result, it is possible to control the pressure conditions in the working spaces via a shared groove in the surface of the valve piston.

In preferred differential pressure motors, the differential pressure motor has a spring element that is supported on a closed outer side of a front surface of a housing that bounds the hollow space, and which is connected to the rod such that the spring element pulls the rod out of the hollow space to a maximum degree without a force effect from a differential pressure.

As a result, the working piston disposed closest to the spring element lies on the inner side of the front surface of the hollow space in the zero load rest position of the differential pressure motor.

Further, the two working pistons have a diameter larger than 10 mm, preferably larger than 20 mm, and very particularly preferred, larger than 30 mm.

As a result, sufficient force transmission is enabled for a differential pressure motor driven with a vacuum or an underpressure in order to also enable normal medical applications.

At least one drive rod is disposed on an outer side of at least one of the two working pistons, wherein the at least one drive rod protrudes out from the housing through a front side and/or a rear side of the housing that bounds the hollow space, and the at least one drive rod is movably supported in a guide in the front side and/or the rear side of the housing, wherein preferably, the rod, which connects the two working pistons, is guided through at least one of the working pistons and there forms the at least one drive rod.

As a result, the movement of the working pistons is directly usable in a simple manner. Preferably, the at least one drive rod is an extension of the rod to which the working pistons are connected. For this purpose, it can preferably be provided that the rod and the at least one drive rod are designed as a single part.

It can also be provided that on the front side of the at least one drive rod a fastening element, in particular a thread, is disposed, via which a tool, such as a saw, a rasp or a brush, with a counter-fastening element that matches the fastening element, in particular a counter-thread that matches the thread, can be affixed to the at least one drive rod.

As a result, a tool can be simply affixed to the at least one drive rod and detached again.

According to a preferred further development, it can also be provided that a housing that bounds the hollow space, the two working pistons, the valve piston and the rod are made of a synthetic material, in particular a thermoplastic synthetic material, preferably using injection molding.

As a result, the differential pressure motor can be used as a hygienic disposable product in sterile surroundings. The synthetic material can be a plastic material.

Further, the geometric dimension of the valve piston in the direction of a connecting line between the two working pistons is smaller than the distance between the two working pistons, wherein preferably, the geometric dimension of the valve piston in the direction of the connecting line between the two working pistons is no more than 50% smaller than the distance between the two working pistons, particularly preferably, no more than 10% smaller than the distance between the two working pistons.

As a result, it is ensured that the valve piston is movable between the two working pistons and can be impacted by the working piston in order to deliver an impulse transmission onto the valve piston and to use the mass inertia of the valve piston to overcome a dead point of the valve.

Further, the differential pressure motor has a starting aid, which prevents the differential pressure motor from stopping at a dead point during an interruption of the supply of the working medium from which it is no longer able to start up on its own accord when the working medium is again supplied to the differential pressure motor, wherein preferably, the starting aid transfers the valve piston into a position in which a differential pressure is able to be generated between the working surfaces of the working pistons by the working medium.

As a result, it is ensured that the valve piston does not remain in a dead point position that prevents renewed start-up of the differential pressure motor.

The decoupling of the force from the differential pressure motor can be achieved via the working pistons or the rod or the drive rod(s). Alternatively, a coupling can also be achieved via magnetic fields, for example when one or both of the working pistons or the drive rod or both drive rods are magnetic. The moving magnetic field can then be used to drive a drive part coupled via the magnetic field and thus a tool outside the differential pressure motor. Further, a current flow in a coil can also be excited.

The objects that form the basis of the present invention are also attained by a surgical drive system comprising a differential pressure motor according to the invention and a valve element, in particular a manually operable valve element, wherein the valve element is disposed in a line that is connected to one of the five openings or to two of the five openings and which is connectible or connected to an underpressure source or a compressed gas reservoir or a pump, so that with the valve element, the connection to the underpressure source, the compressed gas reservoir or the pump is interruptible and/or the pressure at the one opening of the five openings or the two openings of the five openings is adjustable.

The surgical drive system then has the same advantages as the differential pressure motor.

The drive system has a housing with at least one gas-permeable passage that connects the interior space of the housing to the surrounding atmosphere.

Further, a sterile filter is disposed between the valve and the underpressure source.

The surgical drive system has a handle by which a user can hold it in one hand, and the valve element is operable with a trigger on the handle.

As a result, the surgical drive system is suitable for use in a simple manner with one hand.

The surgical drive system has an outer housing that encloses a housing that bounds the hollow space of the differential pressure motor, and which has an opening or a guide through which the rod or a drive rod protrudes from the outer housing.

The objects that form the basis of the present invention are further attained by a medical lavage system for the debridement of soft tissue and/or bone tissue comprising a differential pressure motor according to the invention or a surgical drive system according to the invention, or a medical device for brushing, rasping or sawing soft tissue and/or bone tissue comprising a differential pressure motor according to the invention or a surgical drive system according to the invention.

In the medical field, in particular in the OP field, it makes sense to drive these systems with the differential pressure motor.

The objects that form the basis of the present invention are further attained by a method for operating a differential pressure motor, in which a first working piston and a second working piston are connected via a rod and oscillate linearly in a hollow space, wherein the method comprises the following steps:

A) providing a valve piston, which is disposed in the hollow space between the first working piston and the second working piston, in a first position;

B) providing a connection between a vacuum port and a first working space and a connection between a second working space and the surrounding area of the differential pressure motor in the first position of the valve piston, wherein the first working space is bounded by the first working piston and the second working space is bounded by the second working piston;

C) evacuating gas from the first working space and as a result, moving the first working piston and the second working piston in the hollow space;

D) impacting the valve piston with the second working piston, so that the valve piston is transferred into a second position;

E) providing a connection between the vacuum port and the second working space and a connection between the first working space and the surrounding area of the differential pressure motor in the second position of the valve piston;

F) evacuating gas from the second working space and flowing ambient air into the first working space and as a result, reverse moving the first working piston and the second working piston in the hollow space; and G) impacting the valve piston with the first working piston, so that the valve piston is transferred into the first position.

The objects that form the basis for the present invention are also attained by a method for operating a differential pressure motor, in which a first working piston and a second working piston are connected via a rod and oscillate linearly in a hollow space, wherein the method comprises the following steps:

A) providing a valve piston, which is disposed in the hollow space between the first working piston and the second working piston, in a first position;

B) providing a connection between a compressed gas port and a first working space and a connection between a second working space and the surrounding area of the differential pressure motor in the first position of the valve piston, wherein the first working space is bounded by the first working piston and the second working space is bounded by the second working piston;

C) increasing the gas pressure in the first working space and as a result, moving the first working piston and the second working piston in the hollow space;

D) impacting the valve piston with the first working piston, so that the valve piston is transferred into a second position;

E) providing a connection between the compressed gas port and the second working space and a connection between the first working space and the surrounding area of the differential pressure motor in the second position of the valve piston;

F) increasing the gas pressure in the second working space and flowing compressed gas from the first working space and as a result, reverse moving the first working piston and the second working piston in the hollow space; and G) impacting the valve piston with the second working piston, so that the valve piston is transferred into the first position.

The method is carried out with a differential pressure motor according to the invention or with a surgical drive system according to the invention or with a lavage system according to the invention or a medical device according to the invention for brushing, rasping or sawing soft tissue and/or bone tissue.

Further, the vacuum port or the compressed gas port open out through a first central opening into a valve space in which the valve piston moves, wherein next to the first central opening, a second opening is disposed, which connects the valve space to the first working space, next to the first central opening, a third opening is disposed, which connects the valve space to the second working space, next to the second opening, a fourth outer opening is disposed, which connects the valve space to the surrounding area of the differential pressure motor, and next to the third opening, a fifth outer opening is disposed, which connects the valve space to the surrounding area of the differential pressure motor, wherein three connections, in particular three grooves, are disposed in the valve piston, so that in the first position of the valve piston, the central first opening is connected to the second opening in a gas-permeable manner, and the third opening is connected to the fifth opening in a gas-permeable manner, and in the second position of the valve piston, the central first opening is connected to the third opening in a gas-permeable manner and the second opening is connected to the fourth opening in a gas-permeable manner, wherein preferably, the five openings are otherwise separated from each other by the valve piston.

As a result, the differential pressure motor can be particularly simply constructed and at particularly low cost, and the method can run reliably.

Further, it can be provided that after step G), steps B) to G) are repeated as long as a vacuum or an underpressure is present at the vacuum port, or as long as an overpressure is present at the compressed gas port or a compressed gas introduced.

As a result, the method can be kept running as long as there is sufficient underpressure or sufficient gas pressure. In addition, the differential pressure motor can of course also be stopped by blocking the working pistons, for example by a high resistance against their movement.

Preferably, the movement of the working pistons is used to drive a tool or a pump, in particular a medical tool such as a saw, a rasp or a brush, or to drive a lavage system.

As a result, the movement of the working pistons of the differential pressure motor is available for use by the user.

Further, it is proposed with the present invention that the differential pressure motor is switched on by opening a valve element in a vacuum line at the vacuum port or in a compressed gas line at the compressed gas port and is switched off by closing the valve element.

In this way, the movement of the working piston and thus the differential pressure motor can be stopped in a simple manner.

The invention is based on the surprising finding that by disposing a valve piston between two working pistons, it is possible to provide a simple differential pressure motor that can be produced from synthetic material at low cost and which at the same time runs reliably. The valve piston is a part of a valve with which an alternate impact of different pressures (the first pressure and the second pressure) on the working pistons is controlled. The valve piston can be driven by the working pistons since it is disposed between the working pistons. For this purpose, it is particularly advantageous if the impulse transmitted from the working piston onto the valve piston is sufficient and that the inertia of the valve piston is sufficient, so that the valve piston runs beyond a dead point position in which none of the working pistons is impacted with a compressed gas or with a vacuum or an underpressure. Due to the stroke generated, the working pistons achieve a powerful movement of a tool connected to them, which can be used for different applications in the OP field.

An exemplary differential pressure motor according to the invention is composed of the following components:

a) a first working piston and a second working piston as the two working pistons, which are connected to a rod, wherein the working pistons with the rod are disposed in an axially displaceable manner in an at least partially cylindrical hollow space, b) a valve piston that is disposed in a freely axially displaceable manner between the two working pistons on the rod, wherein the valve piston, together with openings in the hollow space, forms a 2/5-way valve, c) a first working space as a part of the hollow space, in which the first working piston can be moved, d) a second working space as a part of the hollow space, in which the second working piston can be moved, e) wherein the 2/5-way valve is connected to a vacuum line, to the surrounding atmosphere, to the first working space and to the second working space, and wherein f) when subjected to a vacuum, the two working pistons create an oscillating movement of the rod due to periodic changes of the effect of the vacuum and the surrounding atmosphere, wherein the working pistons periodically impact the valve piston and cause an axial movement of the valve piston, as a result of which the valve is switched.

A further exemplary differential pressure motor according to the invention is composed of the following components:

a) an at least partially cylindrical hollow space that is bounded by two closed front surfaces, b) a rod that is disposed in an axially movable manner in the hollow space, wherein the rod protrudes out of the hollow space through recesses in the front surfaces, c) a first working piston that is not displaceably connected to the rod, d) a first working space that is bounded by a front side (working surface) of the first working piston, a cylindrical inner wall of the hollow space and a front surface of the hollow space, e) a second working piston that is not displaceably connected to the rod, f) a second working space that is bounded by a rear side (working surface) of the second working piston, a cylindrical inner wall of the hollow space and a front surface of the hollow space, g) a valve space that is bounded by the rear side of the first working piston, the front side of the second working piston and an at least partially cylindrical inner wall of the hollow space, wherein the hollow space has five openings of a 2/5-way valve in the area of the valve space, which are connected to the valve space in a gas-permeable manner, h) a valve piston, which is disposed in an axially freely movable manner on the rod in the valve space between the first working piston and the second working piston, wherein the valve piston has three circumferential grooves that are axially disposed adjacent to each other, so that they can interact with the five openings of the 2/5-way valve, i) a first opening of the five openings, which is connected to a vacuum supply line or a compressed gas line, which is connected to the 2/5-way valve in a gas-permeable manner, j) a second opening of the five openings in a cylindrical wall of the hollow space or in the first front surface, which is connected to the 2/5-way valve and the first working space, k) a third opening of the five openings in a cylindrical wall of the hollow space or in the second front surface, which is connected to the 2/5-way valve and the second working space, l) two further openings of the five openings in a cylindrical wall of the hollow space, which are connected to the surrounding atmosphere and the 2/5-way valve, m) wherein the axial distance of a first front surface of the valve piston in relation to the rear side of the first working piston is smaller than or equal to the distance of the front side of the first working piston in relation to the inner side of the first front surface of the hollow space, and n) wherein the axial distance of a second front surface of the valve piston in relation to the front side of the second working piston is smaller than or equal to the distance of the rear side of the first working piston in relation to the inner side of the second front surface of the hollow space.

The differential pressure motor according to the invention is preferably used as a drive for lavage systems and devices for the debridement of soft tissue and bone tissue. The differential pressure motor is used as a drive for devices for brushing, rasping and sawing soft tissue and bone tissue. Further, the differential pressure motor is used as a drive for single-use medical devices.

It is to be understood that both the foregoing general description and the following detailed description are exemplary, but are not restrictive, of the disclosure.

BRIEF DESCRIPTION OF THE DRAWING

Below, further exemplary embodiments of the invention will be explained with reference to eleven schematic figures, without thereby limiting the invention. In the figures.

DETAILED DESCRIPTION OF THE DISCLOSURE

Figure 6:
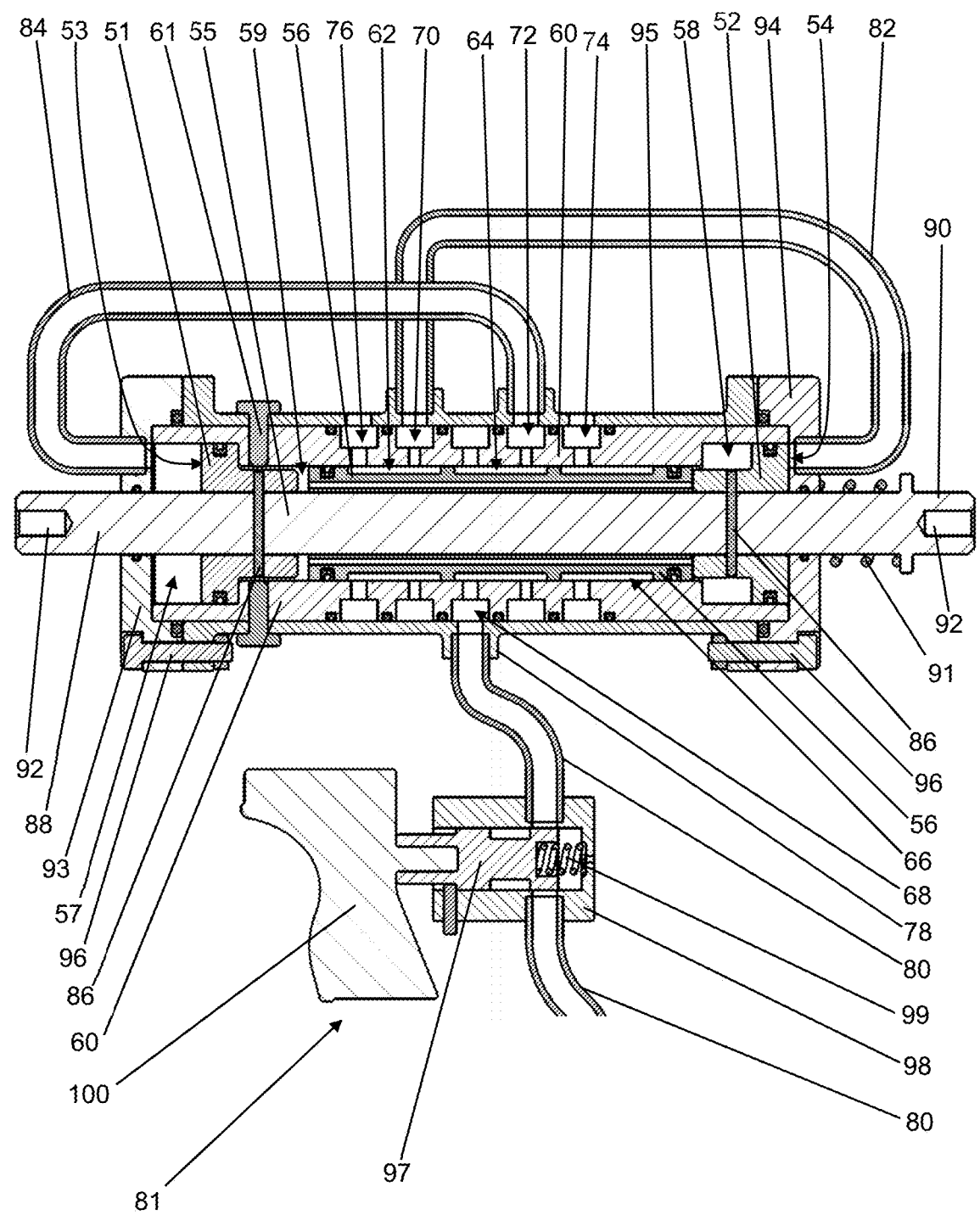
FIG. 6 shows a schematic profile view of a first surgical drive system according to the invention having a second exemplary differential pressure motor according to the invention with a starting aid.
Figure 7:
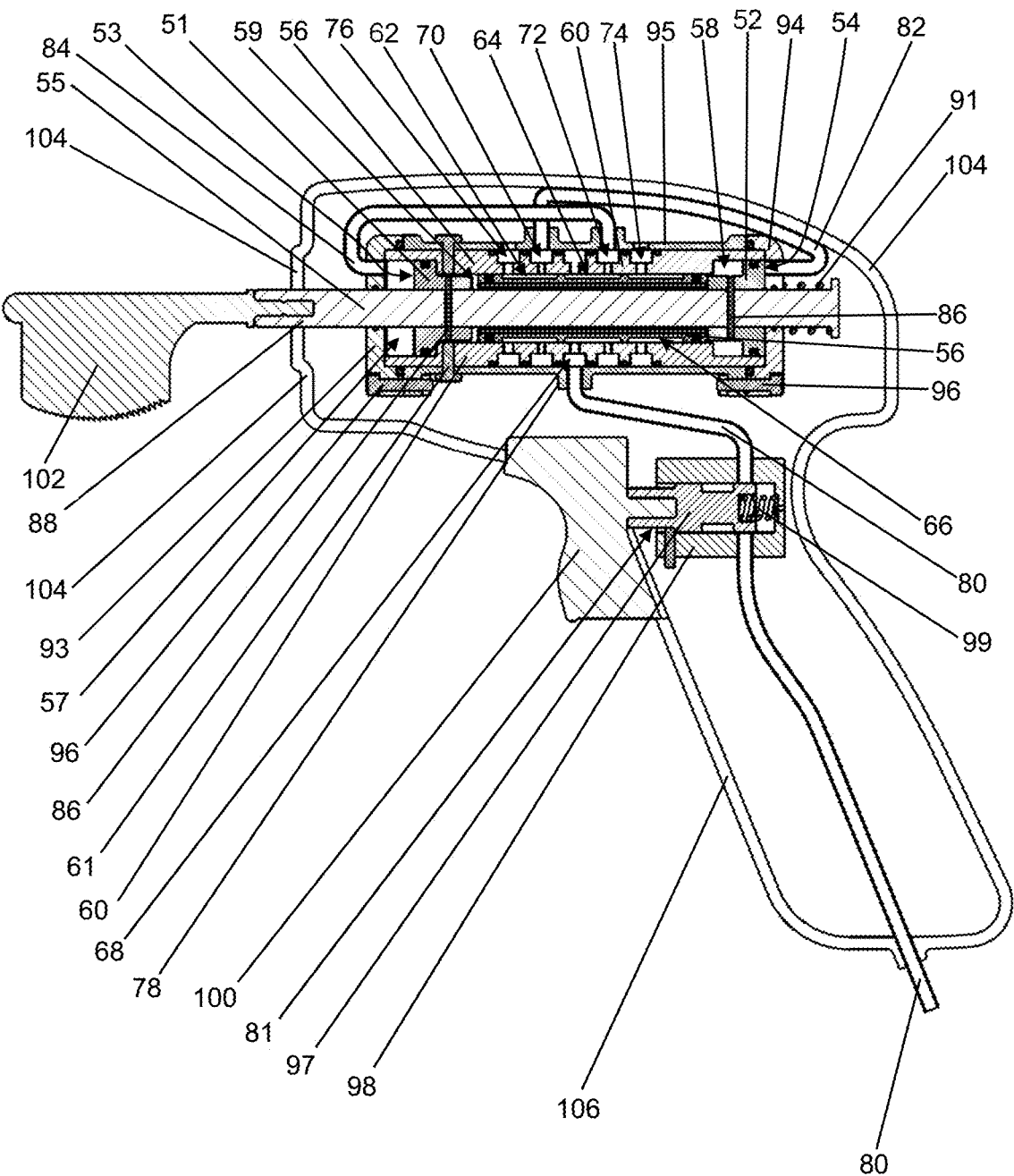
FIG. 7 shows a schematic profile view of a medical device according to the invention for brushing, rasping or sawing soft tissue and/or bone tissue.
Figure 8:
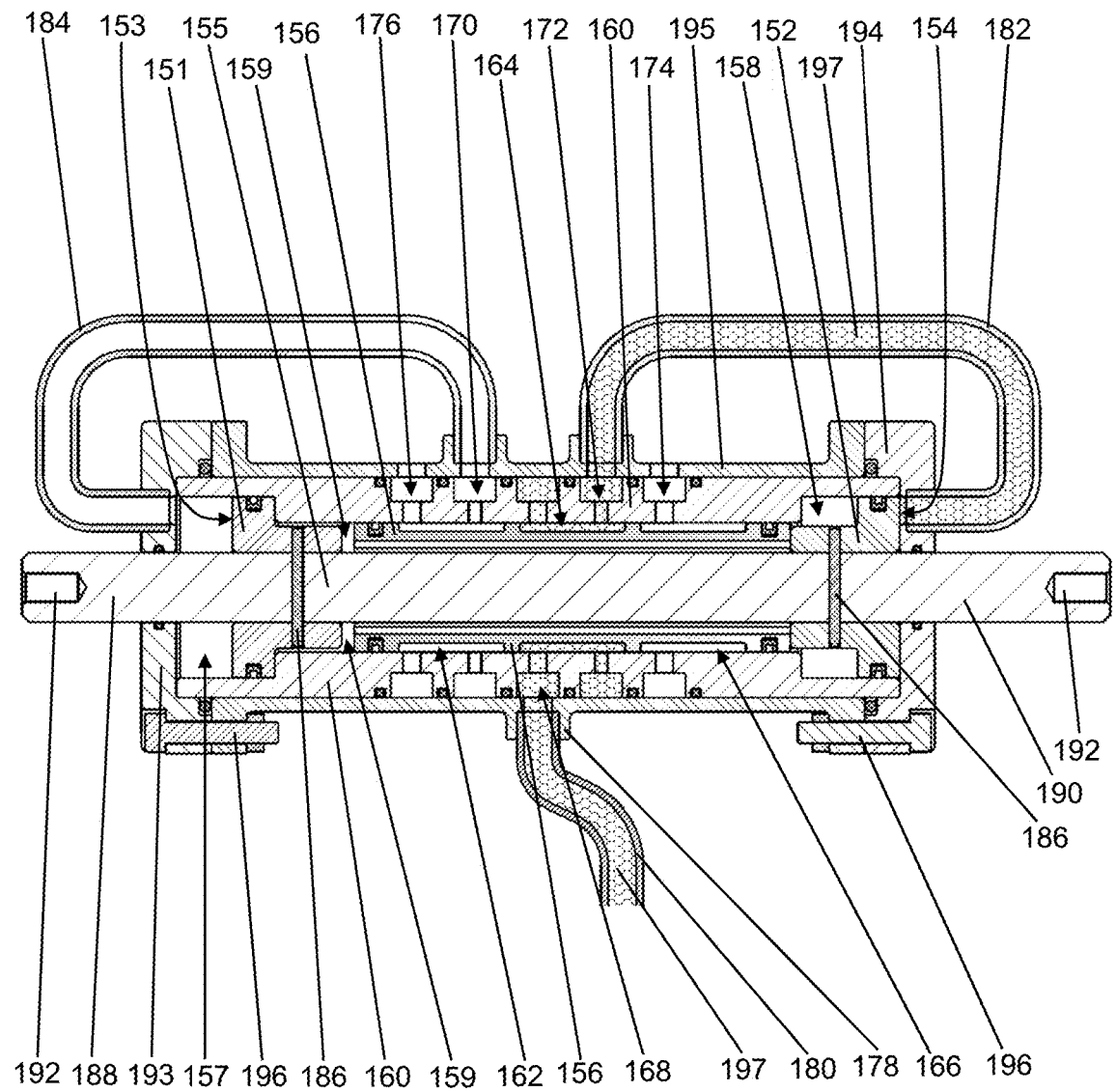
FIG. 8 shows a schematic profile view of a third exemplary differential pressure motor according to the invention during operation with applied compressed gas.
Figure 9:
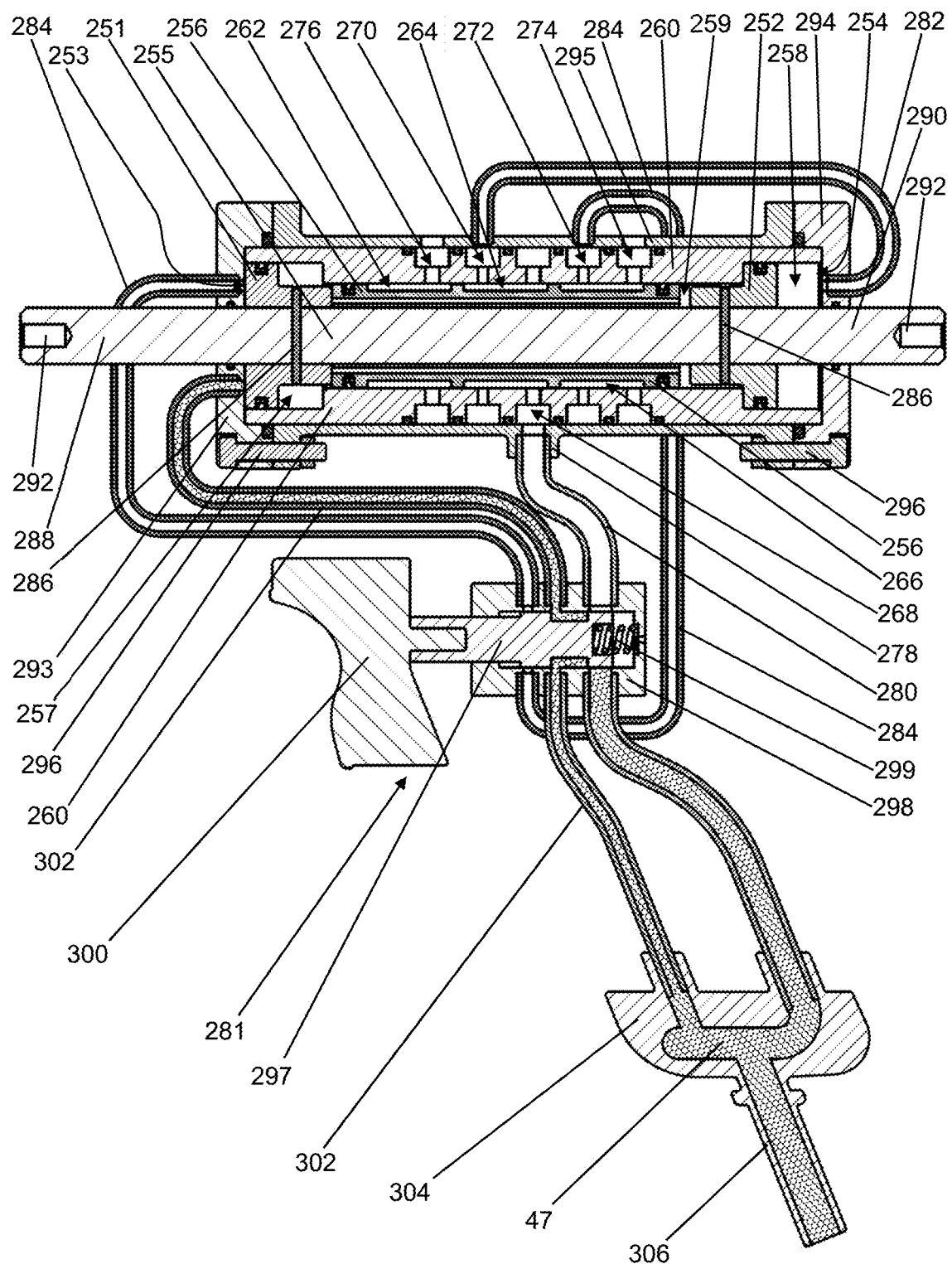
FIG. 9 shows a schematic profile view of a second surgical drive system according to the invention having a fourth exemplary differential pressure motor according to the invention with a starting aid in the initial state.
Figure 10:
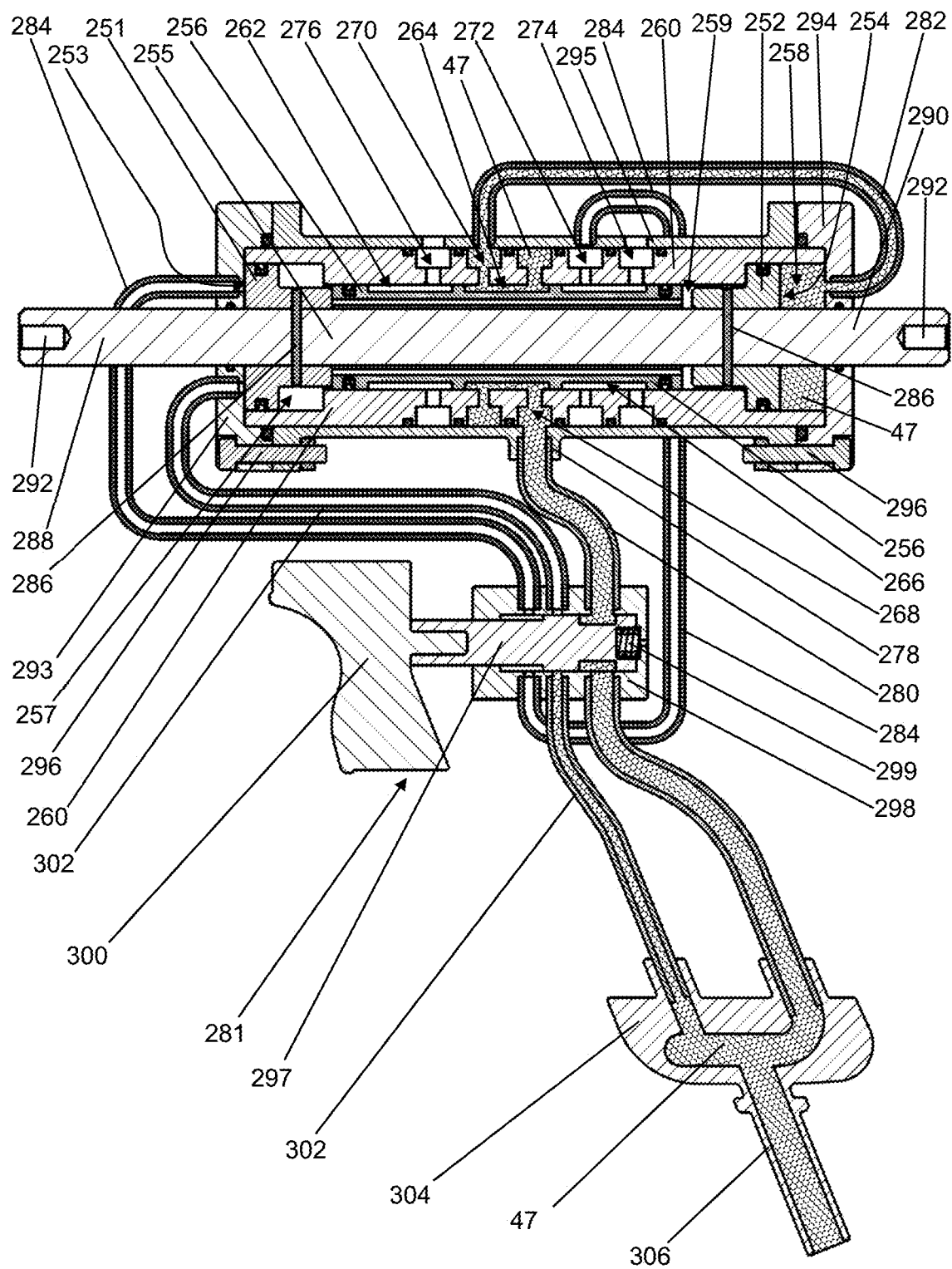
FIG. 10 shows a schematic profile view of the differential pressure motor according to FIG. 9 during operation, wherein the valve piston is transferred into a first position.
Figure 11:
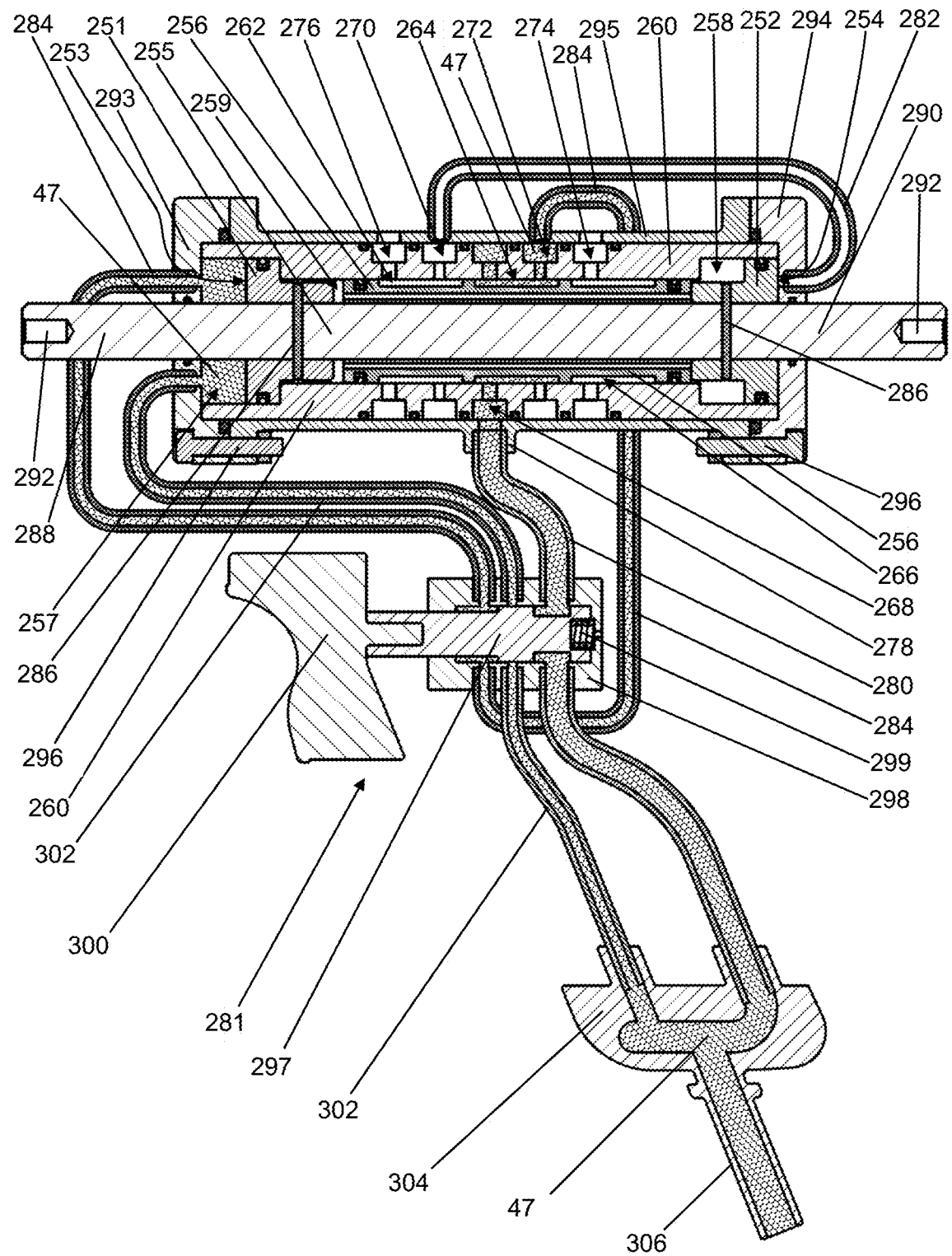
FIG. 11 shows a schematic profile view of the differential pressure motor according to FIGS. 9 and 10 during operation, wherein the valve piston is transferred into a second position.

FIGS. 1 to 5 show profile views of a first exemplary differential pressure motor according to the invention, with which the sequence of a method according to the invention is illustrated. FIGS. 6 and 7 show a surgical drive system according to the invention and a medical device according to the invention with a second differential pressure motor according to the invention. The first exemplary differential pressure motor according to FIGS. 1 to 5 could easily also be used, however, in the surgical drive system according to FIG. 6 and in the medical device according to FIG. 7. FIG. 8 shows a third exemplary differential pressure motor according to the invention, which can be driven with a compressed gas. FIGS. 9 to 11 show a second surgical drive system according to the invention with a fourth exemplary differential pressure motor according to the invention.

The front sides of the differential pressure motors, the surgical drive systems and the medical device are shown on the left in all figures, wherein the differential pressure motors acting on both sides according to FIGS. 1 to 6 and 8 to 11, in addition to a linear oscillating drive on the front side, can generally also be designed to drive a tool or a pump with the rear side.

The first exemplary differential pressure motor according to the invention has a first working piston 1 and a second working piston 2. The first working piston 1 has a working surface 3 that points in the direction of the front side of the differential pressure motor (on the left in FIGS. 1 to 5). In the same way, the second working piston 2 has a working surface 4 that points in the direction of the rear side of the differential pressure motor (on the right in FIGS. 1 to 5). The work on the two working pistons 1, 2 can thus be performed on respective opposite sides, so that the compressed gas motor can be driven on both sides. The first working piston 1 and the second working piston 2 are firmly connected to each other via a rod 5. The rod 5 keeps the two working pistons 1, 2 at a fixed distance apart from each other. Further, the alignment of the working pistons 1, 2 to each other is fixed by the rod 5.

Between the two working pistons 1, 2, a sheath-shaped valve piston 6 is disposed around the rod 5 and is axially movably supported on the rod 5 (in relation to the rod 5). The valve piston 6 is smaller in its axial extension than the distance between the two working pistons 1, 2 determined by the rod 5. As a result, the valve piston 6 is movable between the two working pistons 1, 2. According to the invention, preferably the valve piston 6 is smaller than the distance between the two working pistons 1, 2, in relation to the length of the rod 5 between the two working pistons 1, 2 which determines the distance between the two working pistons 1, 2. As a result, an impulse transmission between the sides of the working pistons 1, 2 facing away from the working surfaces 3, 4 onto the valve piston 6 is made possible by a thrust and the mass inertia of the valve piston 6 can be used to push the valve piston 6 beyond a dead point of a valve constructed with the valve piston 6.

The working pistons 1, 2, the rod 5 and the valve piston 6 are located in a hollow space that is partially cylindrical. The first working piston 1 is disposed in a first cylindrical working space 7. The second working piston 2 is disposed in a second cylindrical working space 8. The valve piston 6 is disposed in a cylindrical valve space 9. The first cylindrical working space 7 and the second cylindrical working space 8 have a larger diameter than the valve space 9 disposed between them. The working pistons 1, 2 are movably disposed in the working spaces 7, 8 in the axial direction. The working pistons 1, 2 have a protrusion with a smaller diameter on the side opposite the respective working surface 3, 4, which extends into the valve space 9. As a result, the working pistons 1, 2 can impact onto the valve piston 6 with their protrusions in the valve space 9. In the area of the working surfaces 3, 4, the working pistons 1, 2 have an outer diameter that matches the inner diameter of the respective working space 7, 8. Preferably, the working pistons 1, 2 seal off the respective working space 7, 8 in a gas-tight or pressure-tight manner. For this purpose, circumferential piston rings (see FIGS. 1 to 5) or other seals can be provided on the outer circumference of the working pistons 1, 2.

The valve piston 6 has a cylindrical shape on the outside that matches the cylindrical valve space 9. On the outer circumference on its two ends facing towards the working pistons 1, 2, the valve piston 6 has one circumferential piston ring each (see FIGS. 1 to 5) or another sealing ring. In the interior of the valve piston 6, a gas-permeable passage is disposed that connects the two sides of the valve piston 6 that face towards the working pistons 1, 2 to each other in a gas-permeable manner.

The two working spaces 7, 8 and the valve space 9 together form the partially cylindrical hollow space in which the working pistons 1, 2 with the rod 5 and the valve piston 6 are movably disposed. The hollow space can be formed by a hollow body made of synthetic material. The hollow space can be bounded by walls 10 of the hollow space.

In an otherwise cylindrical outer circumference of the valve piston 6, three circumferential rotation-symmetric grooves 12, 14, 16 are disposed. These grooves 12, 14, 16, together with the wall 10 that surrounds them, form three ring-shaped hollow spaces that are separated from each other. These can be used to switch a valve that is formed with the valve piston 6. In order to form such a valve, five complete openings 18, 20, 22, 24, 26 are disposed in the wall 10 in the area of the valve space 9. The five complete openings 18, 20, 22, 24, 26 are disposed axially (in relation to the cylindrical valve space 9) adjacent to each other. The first central opening 18 opens out into a vacuum port 28. A vacuum line 30 in the form of a hose can be connected to the vacuum port 28. The vacuum line 30 can connect the vacuum port 28 and thus the first opening 18 to a vacuum source or underpressure source. The second opening 20 that is disposed axially next to the first opening 18 can be connected to the second working space 8 in a gas-permeable manner via a line 32. The third opening 22 that is disposed axially next to the first opening 18 but opposite the second opening 20 can be connected to the first working space 7 in a gas-permeable manner via a line 34. The fourth outer opening 24 can be connected to the area surrounding the differential pressure motor in a gas-permeable manner. The fifth outer opening 26 can be connected to the area surrounding the differential pressure motor in a gas-permeable manner.

The complete openings 18, 20, 22, 24, 26 that lie axially adjacent to each other, together with the wall 10 and the valve piston 6 that is axially movable within the valve space 9 and sealed against the wall 10, and also the grooves 12, 14, 16, can form the valve by which the differential pressure motor is controlled. The movement of the valve piston 6 can be initiated by the working pistons 1, 2 that impact the valve piston 6 from both sides and can thus excite an oscillation. The grooves 12, 14, 16 can preferably be so broad that in each case, two adjacent openings 18, 20, 22, 24, 26 simultaneously open out into one of the grooves 12, 14, 16. As a result, depending on the position of the valve piston 6, two openings 18, 20, 22, 24, 26 can always be connected to each other in a gas-permeable manner. The grooves 12, 14, 16 are preferably not so broad in the axial direction, however, that three openings 18, 20, 22, 24, 26 can open out into the same groove 12, 14, 16. Further, preferably, the wall 10 between the grooves 12, 14, 16 can be sufficiently broad in the axial direction that it can at least just cover the second opening 20 and the third opening 22 such that the possibility is excluded that the second opening 20 or the third opening 22 can open out simultaneously into two of the grooves 12, 14, 16 and thus cause a "short circuit" of the differential pressure motor. For this reason, it is also important that the valve piston 6, in particular due to its inertia, automatically travels over the point at which the second opening 20 or the third opening 22 are closed and do not open out into any of the grooves 12, 14, 16. As a result, a dead point position of the differential pressure motor is avoided.

In a first position of the valve piston 6 (see FIG. 4), the first central opening 18 and the adjacent second opening 20 are interconnected in a gas-conductive manner via the central groove 14, and the third opening 22 and the adjacent fourth opening 24 on the edge side are interconnected in a gas-conductive manner via the rear groove 16, and the five openings 18, 20, 22, 24, 26 are otherwise separated from each other in a gas-tight manner by the valve. In a second position of the valve piston 6 (see FIG. 5), the first central opening 18 and the third opening 22 are interconnected in a gas-conductive manner via the central groove 14, and the second opening 20 and the adjacent fifth opening 26 on the edge side are interconnected in a gas-conductive manner via the front groove 12, and the five openings 18, 20, 22, 24, 26 are otherwise separated from each other in a gas-tight manner by the valve. The valve piston 6 can be transferred from the first position into the second position by the working pistons 1, 2. When a vacuum 47 acts on the vacuum port 28, the second working space 8 can be evacuated in the first position of the valve piston 6. At the same time, the first working space 7 can be connected to the surrounding area in a gas-permeable manner via the third opening 22, the fourth opening 24 and the rear groove 16, so that air flows into or is present in the first working space 7. Due to this pressure difference, the first working piston 1 can be pushed backward, or the second working piston 2 can be pulled backward (to the right in FIGS. 1 to 5). When the first working piston 1, which is connected to the second working piston 2 via the rod 5, is pulled backward, it impacts the valve piston 6. As a result, the valve piston 6 can be thrust out of the first position and transferred into the second position. In this second position of the valve piston 6 (see FIG. 5), the first working space 7 can be evacuated, while it is separated from the surrounding area. At the same time, the second working space 8 can be connected to the surrounding area in a gas-permeable manner via the second opening 20, the fifth opening 26 and the front groove 12, so that air flows into the second working space 8 and thus, the second working piston 2 is pushed forward or the first working piston 1 is pulled forward (to the left in FIGS. 1 to 5). As a result, a periodic linear movement or oscillation of the working pistons 1, 2 and the valve piston 6 can be generated. This movement is driven by the vacuum or the underpressure as the first pressure and by the surrounding air pressure as the second pressure. Alternatively, the vacuum port 28 can also lie open and a compressed gas source with a pressure higher than the surrounding air pressure can be connected to the fourth opening 24 and the fifth opening 26. The functional principle remains the same. In order to achieve sufficient power of the differential pressure motor, a sufficient differential pressure between the first pressure and the second pressure must be ensured. In addition, an increase in the power of the differential pressure motor can also be achieved by enlarging the working surfaces 3, 4.

Figure 1:
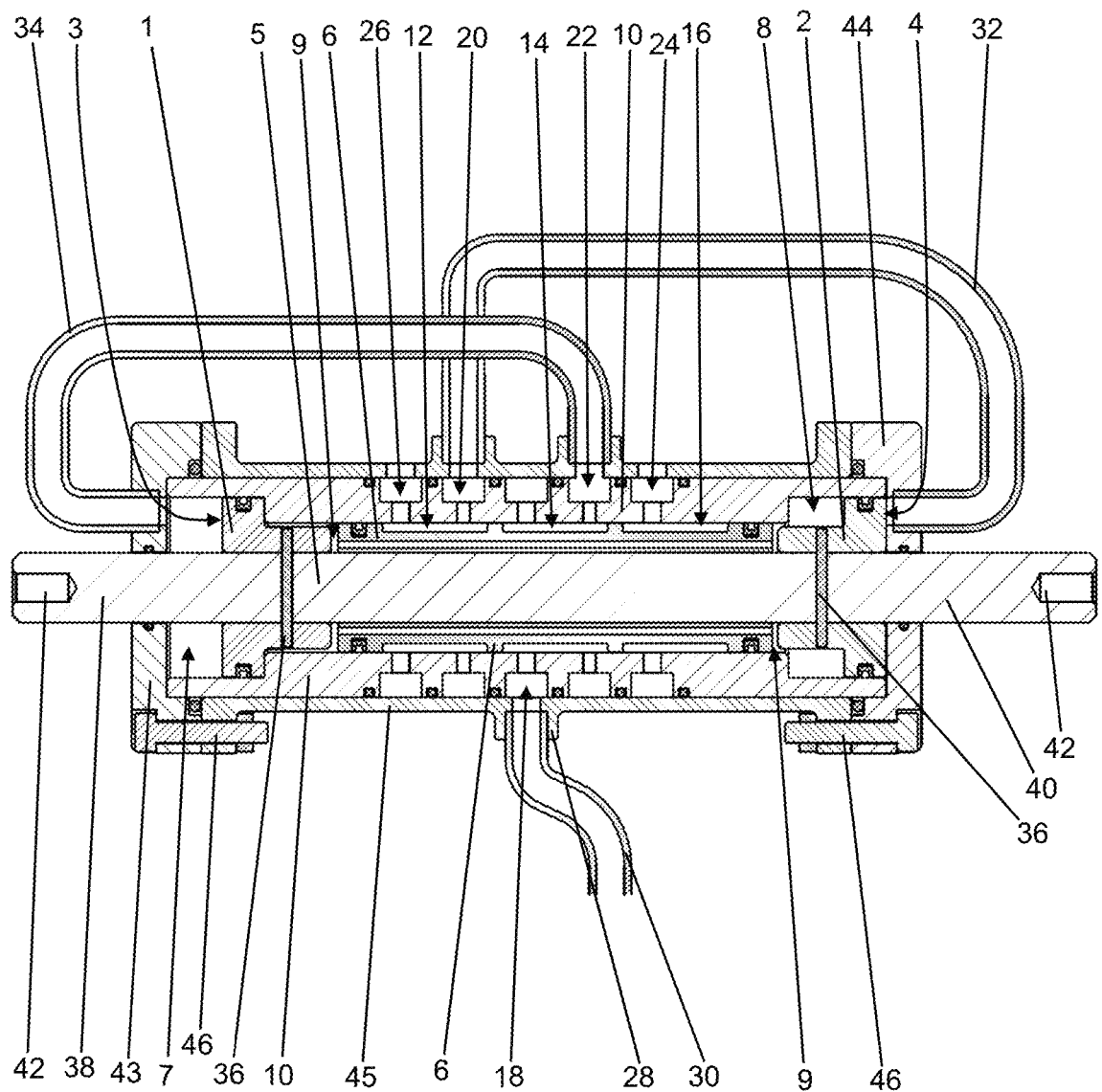
FIG. 1 shows a schematic profile view of a first exemplary differential pressure motor according to the invention at a standstill.
Figure 2:
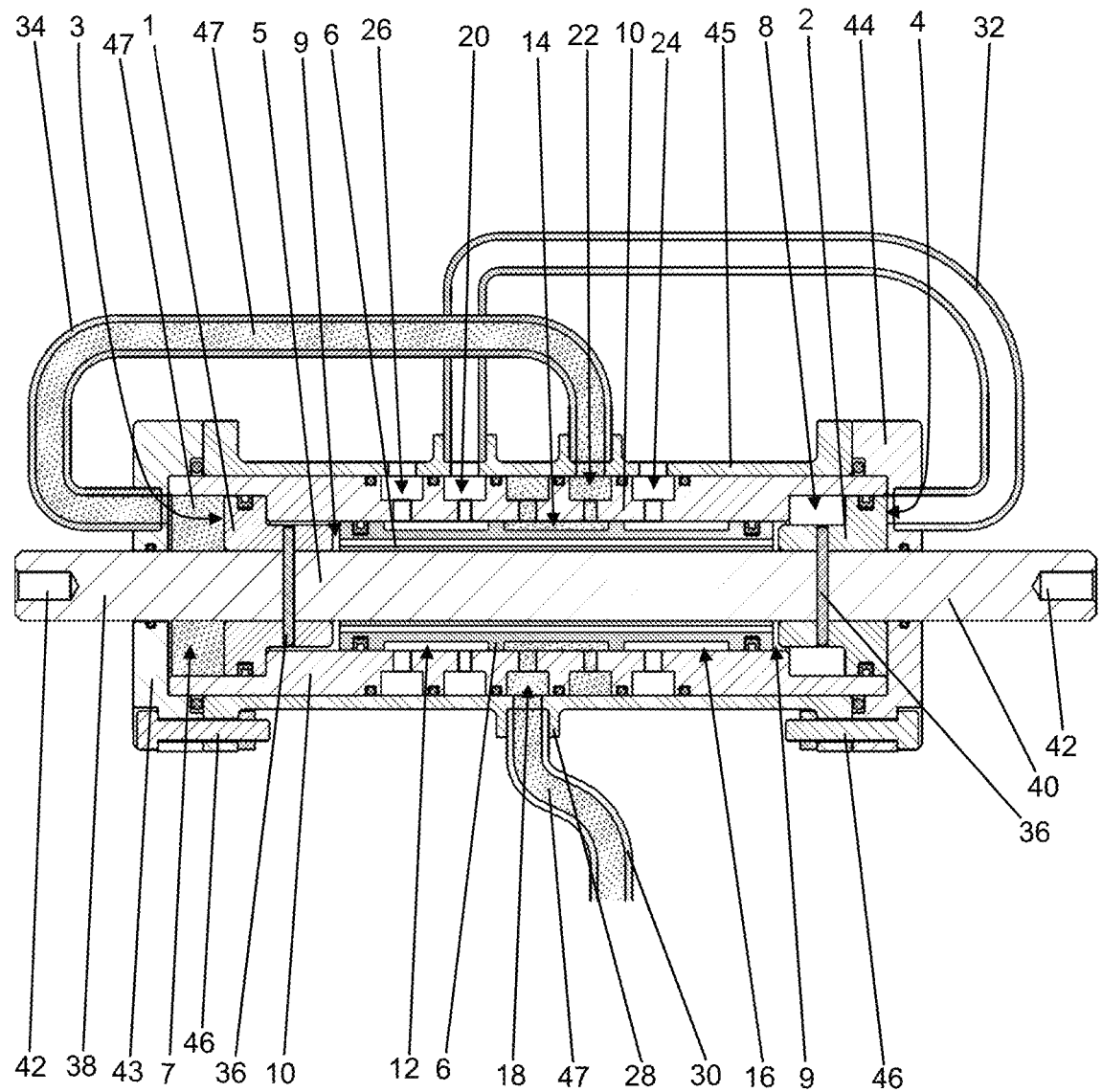
FIG. 2 shows a schematic profile view of the differential pressure motor according to FIG. 1 with a vacuum applied.
Figure 3:
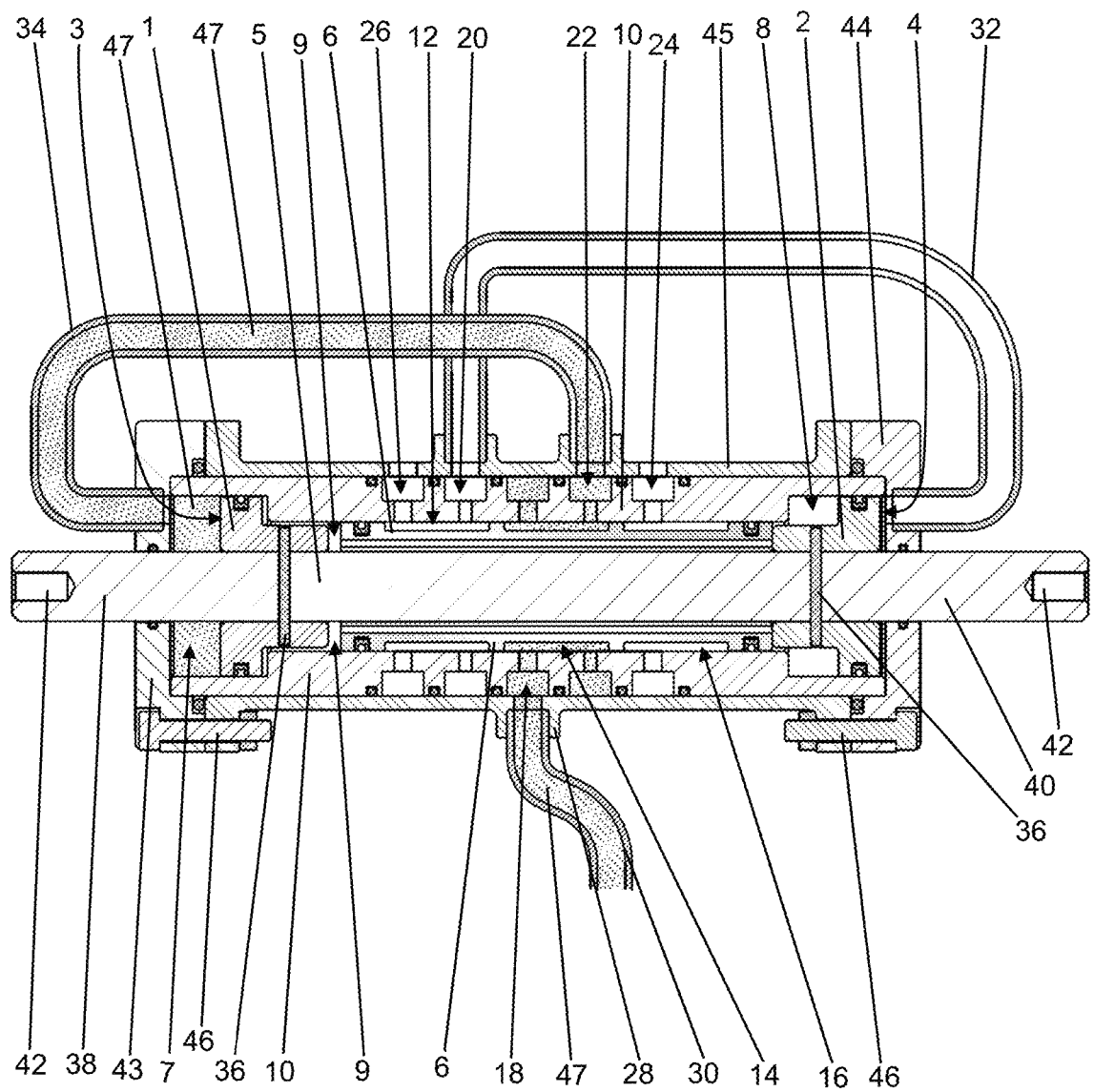
FIG. 3 shows a schematic profile view of the differential pressure motor according to FIGS. 1 and 2 when the second working piston impacts on the valve piston.
Figure 4:
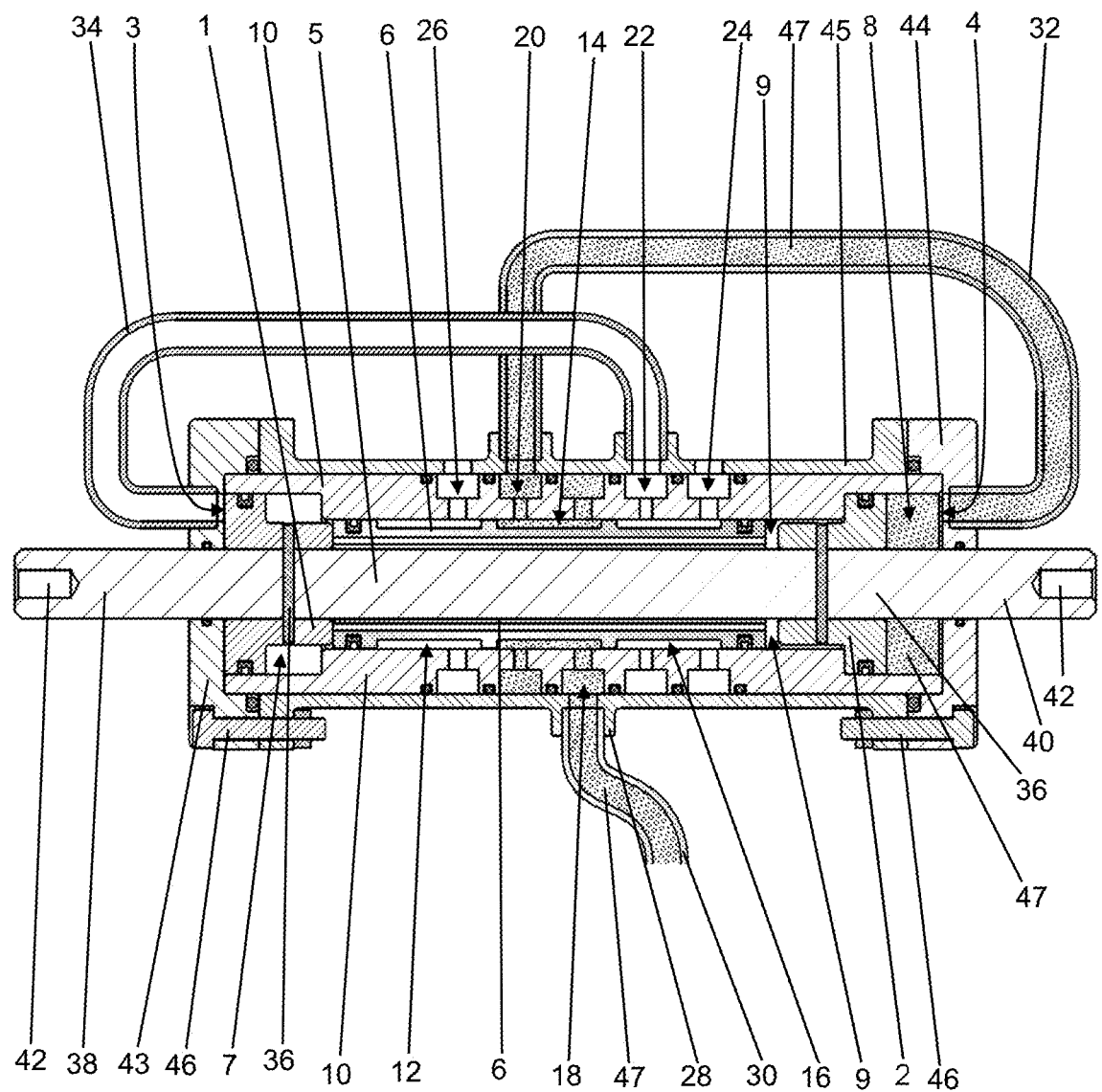
FIG. 4 shows a schematic profile view of the differential pressure motor according to FIGS. 1 to 3 during operation, wherein the valve piston is transferred into a first position.
Figure 5:
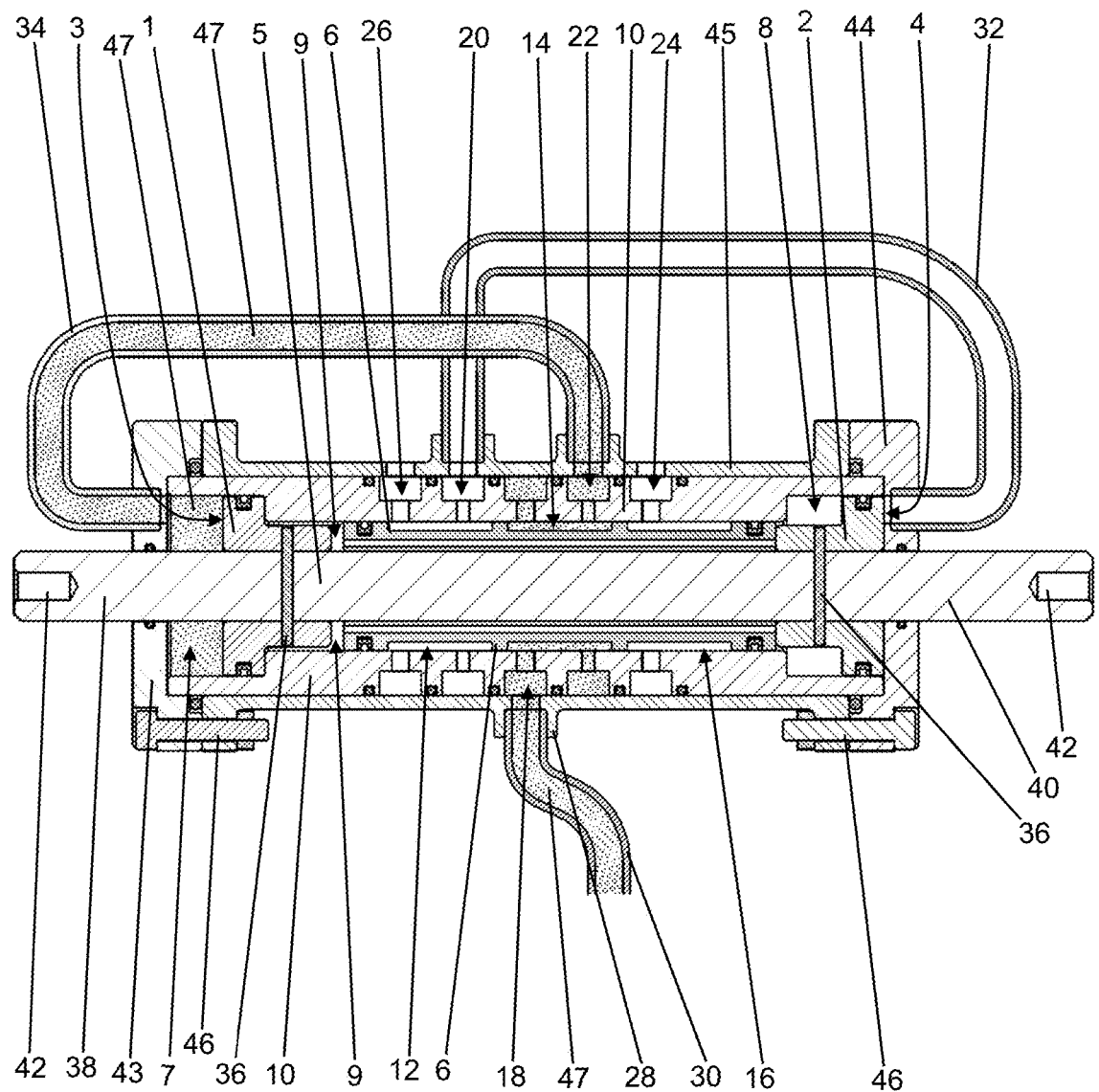
FIG. 5 shows a schematic profile view of the differential pressure motor according to FIGS. 1 to 4 during operation, wherein the valve piston is transferred into a second position.

When the differential pressure motor is at a standstill (see FIG. 1), the vacuum 47 can be applied to the vacuum port 28 (see FIG. 2). Here, the first working space 3 can be evacuated, while the second working space 4 is open outward. Due to the pressure difference between the first working space 3 and the second working space 4, the working pistons 1, 2 can be driven forward with the rod 5 until the second working piston 2 impacts the valve piston 6 in the valve space 9 (see FIG. 3). Here, the second working piston 2 can push the valve piston 6 forward and thus set the differential pressure motor in motion.

The working pistons 1, 2 can be connected to the rod 5 via bolts 36. As a result, the assembly of the differential pressure motor is made easier. The rod 5 can extend through the two working pistons 1, 2. As a result, a first drive rod 38 protrudes on the front side of the first working piston 1, and a second drive rod 40 protrudes on the rear side of the second working piston 2, which are able to drive tools or a pump (not shown in FIGS. 1 to 5). For this purpose, one fastening element 42 each can be disposed on the ends of the drive rods 38, 40. The fastening element 42 can take the form of a square hole or a threaded bore, which can be connected to a matching counter-fastening element on a tool.

The first working space 3 is closed on its front side with a closure 43 made of synthetic material, which forms a front surface of the first working space 7. The first drive rod 38 can be guided through the closure 43. The closure 43 can be sealed against the first drive rod 38 with a sealing ring, through which the first drive rod 38 can slide. The second working space 8 is closed on its front side with a closure 44 made of synthetic material, which forms a front surface of the second working space 8. The second drive rod 40 can be guided through the closure 44. The closure 44 can be sealed against the second drive rod 40 with a sealing ring, through which the second drive rod 40 can slide.

The differential pressure motor further has an outer shell 45 made of synthetic material, which encloses the walls 10. The closures 43, 44 can be screwed onto the outer shell 45 with screws 46, wherein one sealing ring can be provided in each case for the purpose of sealing between the closures 43, 44 and the outer shell 45. The openings 18, 20, 22, 24, 26 are sealed against the outer shell 45 with seals. The outer shell 45 can also form the vacuum port 28 and preferably also be used to form ports for the connection of the second opening 20 with the line 32 to the second working space 8 and for the connection of the third opening 22 with the line 34 to the first working space 7.

FIGS. 6 and 7 show a first surgical drive system according to the invention and a medical device according to the invention with a second differential pressure motor according to the invention, wherein the differential pressure motor according to the second exemplary embodiment, in contrast to the differential pressure motor according to the first exemplary embodiment according to FIGS. 1 to 5, has a starting aid in the form of a tensioned spring element 91, which ensures problem-free starting up of the differential pressure motor.

The second exemplary differential pressure motor according to the invention has a first working piston 51 and a second working piston 52. The first working piston 51 has a working surface 53 that points in the direction of the front side of the differential pressure motor (on the left in FIGS. 6 and 7). In the same way, the second working piston 52 has a working surface 54 that points in the direction of the rear side of the differential pressure motor (on the right in FIGS. 6 and 7). The work on the two working pistons 51, 52 can thus be performed on respective opposite sides, so that the compressed gas motor can be driven on both sides. The first working piston 51 and the second working piston 52 are firmly connected to each other via a rod 55. The rod 55 keeps the two working pistons 51, 52 at a fixed distance apart from each other. Further, the alignment of the working pistons 51, 52 to each other is fixed by the rod 55.

Between the two working pistons 51, 52, a sheath-shaped valve piston 56 is disposed around the rod 55 and is axially movably supported on the rod 55 (in relation to the rod 55). The valve piston 56 is smaller in its axial extension than the distance between the two working pistons 51, 52 determined by the rod 55. As a result, the valve piston 56 can be moved between the two working pistons 51, 52. According to the invention, the valve piston 56 is smaller than the distance between the two working pistons 51, 52, in relation to the length of the rod 55 between the two working pistons 51, 52 that determines the distance between the two working pistons 51, 52. As a result, an impulse transmission between the sides of the working pistons 51, 52 facing away from the working surfaces 53, 54 onto the valve piston 56 is made possible by a thrust and the mass inertia of the valve piston 56 can be used to push the valve piston 56 beyond a dead point of a valve constructed with the valve piston 56.

The working pistons 51, 52, the rod 55 and the valve piston 56 are located in a hollow space that is partially cylindrical. The first working piston 51 is disposed in a first cylindrical working space 57. The second working piston 52 is disposed in a second cylindrical working space 58. The valve piston 56 is disposed in a cylindrical valve space 59. The first cylindrical working space 57 and the second cylindrical working space 58 have a larger diameter than the valve space 59 disposed between them. The working pistons 51, 52 are movably disposed in the working spaces 57, 58 in the axial direction. The working pistons 51, 52 have a protrusion with a smaller diameter on the side opposite the respective working surface 53, 54, which extends into the valve space 59. As a result, the working pistons 51, 52 can impact onto the valve piston 56 with their protrusions in the valve space 59. In the area of the working surfaces 53, 54, the working pistons 51, 52 have an outer diameter that matches the inner diameter of the respective working space 57, 58. Preferably, the working pistons 51, 52 seal off the respective working space 57, 58 in a gas-tight or pressure-tight manner. For this purpose, circumferential piston rings (see FIGS. 6 and 7) or other seals can be provided on the outer circumference of the working pistons 51, 52.

The valve piston 56 has a cylindrical shape on the outside that matches the cylindrical valve space 59. On the outer circumference on its two ends facing towards the working pistons 51, 52, the valve piston 56 has one circumferential piston ring each (see FIGS. 6 and 7) or another sealing ring. In the interior of the valve piston 56, a gas-permeable passage is disposed that connects the two sides of the valve piston 56 that face toward the working pistons 51, 52 to each other in a gas-permeable manner.

The two working spaces 57, 58 and the valve space 59 together form the partially cylindrical hollow space in which the working pistons 51, 52 with the rod 55 and the valve piston 56 are movably disposed. The hollow space can be formed by a hollow body made of synthetic material. The hollow space can be bounded by walls 60 of the hollow space.

In an otherwise cylindrical outer circumference of the valve piston 56, three circumferential rotation-symmetric grooves 62, 64, 66 are disposed. These grooves 62, 64, 66, together with the wall 60 that surrounds them, form three ring-shaped hollow spaces that are separated from each other. These can be used to switch a valve that is formed with the valve piston 56. In order to form such a valve, five complete openings 68, 70, 72, 74, 76 are disposed in the wall 60 in the area of the valve space 59. The five complete openings 68, 70, 72, 74, 76 are disposed axially (in relation to the cylindrical valve space 59) adjacent to each other. The first central opening 68 opens into a vacuum port 78. A vacuum line 80 in the form of a hose can be connected to the vacuum port 78. The vacuum line 80 can connect the vacuum port 78 and thus the first opening 68 to a vacuum source or underpressure source. The second opening 70 is disposed axially next to the first opening 68 and connected to the second working space 58 in a gas-permeable manner via a line 82. The third opening 72 is disposed axially next to the first opening 68 but opposite the second opening 70 and connected to the first working space 57 in a gas-permeable manner via a line 84. The fourth outer opening 74 is connected to the area surrounding the differential pressure motor in a gas-permeable manner. The fifth outer opening 76 is connected to the area surrounding the differential pressure motor in a gas-permeable manner.

The complete openings 68, 70, 72, 74, 76 that lie axially adjacent to each other, together with the wall 60 and the valve piston 56 that is axially movable within the valve space 59 and sealed against the wall 60, and also the grooves 62, 64, 66, form the valve by which the differential pressure motor is controlled. The movement of the valve piston 56 can be initiated by the working pistons 51, 52 that impact the valve piston 56 from both sides and can thus excite an oscillation. The grooves 62, 64, 66 preferably are so broad that in each case, two adjacent openings 68, 70, 72, 74, 76 simultaneously open out into one of the grooves 62, 64, 66. As a result, depending on the position of the valve piston 56, two openings 68, 70, 72, 74, 76 can always be connected to each other in a gas-permeable manner. The grooves 62, 64, 66 are preferably not so broad in the axial direction, however, that three openings 68, 70, 72, 74, 76 can open out into the same groove 62, 64, 66. Further, preferably, the wall 60 between the grooves 62, 64, 66 is sufficiently broad in the axial direction that it at least just covers the second opening 70 and the third opening 72 such that the possibility is excluded that the second opening 70 or the third opening 72 can open out simultaneously into two of the grooves 62, 64, 66 and thus cause a "short circuit" of the differential pressure motor. For this reason, it is also important that the valve piston 56, in particular due to its inertia, automatically travels over the point at which the second opening 70 or the third opening 72 are closed and do not open out into any of the grooves 62, 64, 66. As a result, a dead point position of the differential pressure motor is avoided.

In a first position of the valve piston 56, the first central opening 68 and the adjacent second opening 70 are interconnected in a gas-conductive manner via the central groove 64, and the third opening 72 and the adjacent fourth opening 74 on the edge side are interconnected in a gas-conductive manner via the rear groove 66, and the five openings 68, 70, 72, 74, 76 are otherwise separated from each other in a gas-tight manner by the valve. In a second position of the valve piston 56 (see FIGS. 6 and 7), the first central opening 68 and the third opening 72 are interconnected in a gas-conductive manner via the central groove 64, and the second opening 70 and the adjacent fifth opening 76 on the edge side are interconnected in a gas-conductive manner via the front groove 62, and the five openings 68, 70, 72, 74, 76 are otherwise separated from each other in a gas-tight manner by the valve. The valve piston 56 can be transferred from the first position into the second position by the working pistons 51, 52. When a vacuum acts on the vacuum port 78, the second working space 58 can be evacuated in the first position of the valve piston 56. At the same time, the first working space 57 can be connected to the surrounding area in a gas-permeable manner via the third opening 72, the fourth opening 74 and the rear groove 66, so that air flows into or is present in the first working space 57. Due to this pressure difference, the first working piston 51 can be pushed backward, or the second working piston 52 can be pulled backward (to the right in FIGS. 6 and 7). When the first working piston 51, which is connected to the second working piston 52 via the rod 55, is pulled backward, it impacts the valve piston 56. As a result, the valve piston 56 can be thrust out of the first position and transferred into the second position. In this second position of the valve piston 56 (see FIGS. 6 and 7), the first working space 57 can be evacuated, while it is separated from the surrounding area. At the same time, the second working space 58 can be connected to the surrounding area in a gas-permeable manner via the second opening 70, the fifth opening 76 and the front groove 62, so that air flows into the second working space 58 and thus, the second working piston 52 is pushed forward or the first working piston 51 is pulled forward (to the left in FIGS. 6 and 7). As a result, a periodic linear movement or oscillation of the working pistons 51, 52 and the valve piston 56 can be generated. This movement is driven by the vacuum or the underpressure as the first pressure and by the surrounding air pressure as the second pressure. Alternatively, the vacuum port 78 can also lie open and a compressed gas source with a pressure higher than the surrounding air pressure can be connected to the fourth opening 74 and the fifth opening 76. The functional principle remains the same. In order to achieve sufficient power of the differential pressure motor, a sufficient differential pressure between the first pressure and the second pressure must be ensured. In addition, an increase in the power of the differential pressure motor can also be achieved by enlarging the working surfaces 53, 54.

When the differential pressure motor is at a standstill, the spring element 91, which can be disposed as a compression spring between a closure 94 made of synthetic material that bounds the rear side of the second working space 58 and a protruding ring disk on the rod 55, can pull back the rod 55 and the working pistons 51, 52. As a result, the valve piston 56 is also automatically brought into a second position. The differential pressure motor is thus prevented from coming to a standstill at a dead point and being unable to re-start.

The working pistons 51, 52 can be connected to the rod 55 via bolts 86. In order to be able to mount the bolt 86 for the first working piston 51 without problems, a passage is provided that can be closed by two plugs 61 after mounting. As a result, the assembly of the differential pressure motor is made easier. The rod 55 extends through the two working pistons 51, 52. As a result, a first drive rod 88 protrudes on the front side of the first working piston 51. A second drive rod 90 protrudes on the rear side of the second working piston 52 (see FIG. 6). However, the second drive rod 90 can also be omitted (see FIG. 7). The drive rods 88, 90 can be used to drive tools such as a saw 102 (see FIG. 7) or a pump. For this purpose, one fastening element 92 each can be disposed on the ends of the drive rods 88, 90. The fastening element 92 can take the form of a square hole or a threaded bore, which can be connected to a matching counter-fastening element on a tool.

The first working space 53 is closed on its front side with a closure 93 made of synthetic material, which forms a front surface of the first working space 57. The first drive rod 88 is guided through the closure 93. The closure 93 is sealed against the first drive rod 88 with a sealing ring, through which the first drive rod 88 slides. The second working space 58 is closed on its front side with the closure 94, which forms a front surface of the second working space 58. The second drive rod 90 is guided through the closure 94. The closure 94 is sealed against the second drive rod 90 with a sealing ring, through which the second drive rod 90 slides.

The differential pressure motor further has an outer shell 95 made of synthetic material, which encloses the walls 60. The closures 93, 94 can be screwed onto the outer shell 95 with screws 96, wherein one sealing ring can be provided in each case for the purpose of sealing between the closures 93, 94 and the outer shell 95. The openings 68, 70, 72, 74, 76 are sealed against the outer shell 95 with seals. The outer shell 95 can also form the vacuum port 78 and preferably also be used to form ports for the connection of the second opening 70 with the line 82 to the second working space 58 and for the connection of the third opening 72 with the line 84 to the first working space 57.

In the vacuum line 80 of the surgical drive system according to FIG. 6, or the medical device according to FIG. 7, a manually operable valve element 81 is disposed, with which the connection between the vacuum port 78 and the vacuum source or the underpressure source can be interrupted. The valve element 81 has a valve body 97, which is supported in a valve housing 98 in a linearly displaceable manner. A spring 99 in the valve housing 98 presses the valve body 97 into a closed position. A trigger 100 can be used to press the valve body 97 against the spring 99 into the open position, and thus the differential pressure motor can be started up.

The medical device according to the invention for brushing, rasping or sawing soft tissue and/or bone tissue according to FIG. 7 can also have a housing 104 made of synthetic material, in which the differential pressure motor and the valve element 81 are disposed. The housing 104 can be formed as a handle 106 on its lower side (below in FIG. 7). The device can then be held in one hand by the handle 106 and the trigger 100 can be operated with the same hand.

FIG. 8 shows a schematic profile view of a third exemplary differential pressure motor according to the invention during operation with applied compressed gas 197. The differential pressure motor driven with compressed gas 197 can be used to construct a surgical drive system with which in turn a medical device is constructed in the same way as the exemplary embodiment according to FIG. 7. For this purpose, only one valve (in the same way as the valve element 81 shown in FIGS. 6 and 7, but not shown in FIG. 8) needs to be installed in a compressed gas line 180, via which the compressed gas 197 is supplied into the differential pressure motor as a drive fluid. The differential pressure motor according to FIG. 8 has no starting aid, but could easily be designed with such an aid.

The third exemplary differential pressure motor according to the invention has a first working piston 151 and a second working piston 152. The first working piston 151 has a working surface 153 that points in the direction of the front side of the differential pressure motor (on the left in FIG. 8). In the same way, the second working piston 152 has a working surface 154 that points in the direction of the rear side of the differential pressure motor (on the right in FIG. 8). The work on the two working pistons 151, 152 can thus be performed on respective opposite sides, so that the compressed gas motor can be driven on both sides. The first working piston 151 and the second working piston 152 are firmly connected to each other via a rod 155. The rod 155 keeps the two working pistons 151, 152 at a fixed distance apart from each other. Further, the alignment of the working pistons 151, 152 to each other is fixed by the rod 155.

Between the two working pistons 151, 152, a sheath-shaped valve piston 156 is disposed around the rod 155 and is axially movably supported on the rod 155 (in relation to the rod 155). The valve piston 156 is smaller in its axial extension than the distance between the two working pistons 151, 152 determined by the rod 155. As a result, the valve piston 156 can move between the two working pistons 151, 152. According to the invention, preferably the valve piston 156 is smaller than the distance between the two working pistons 151, 152, in relation to the length of the rod 155 between the two working pistons 151, 152 that determines the distance between the two working pistons 151, 152. As a result, an impulse transmission between the sides of the working pistons 151, 152 facing away from the working surfaces 153, 154 onto the valve piston 156 is made possible by a thrust and the mass inertia of the valve piston 156 can be used to push the valve piston 156 beyond a dead point of a valve constructed with the valve piston 156.

The working pistons 151, 152, the rod 155 and the valve piston 156 are located in a hollow space that is partially cylindrical. The first working piston 151 is disposed in a first cylindrical working space 157. The second working piston 152 is disposed in a second cylindrical working space 158. The valve piston 156 is disposed in a cylindrical valve space 159. The first cylindrical working space 157 and the second cylindrical working space 158 have a larger diameter than the valve space 159 disposed between them. The working pistons 151, 152 are movably disposed in the working spaces 157, 158 in the axial direction. The working pistons 151, 152 have a protrusion with a smaller diameter on the side opposite the respective working surface 153, 154, which extends into the valve space 159. As a result, the working pistons 151, 152 can impact onto the valve piston 156 with their protrusions in the valve space 159. In the area of the working surfaces 153, 154, the working pistons 151, 152 have an outer diameter that matches the inner diameter of the respective working space 157, 158. Preferably, the working pistons seal off the respective working space 157, 158 in a gas-tight or pressure-tight manner. For this purpose, circumferential piston rings (see FIG. 8) or other seals can be provided on the outer circumference of the working pistons 151, 152.

The valve piston 156 has a cylindrical shape on the outside that matches the cylindrical valve space 159. On the outer circumference on its two ends facing towards the working pistons 151, 152, the valve piston 156 has one circumferential piston ring each (see FIG. 8) or another sealing ring. In the interior of the valve piston 156, a gas-permeable passage is disposed that connects the two sides of the valve piston 156 that face toward the working pistons 151, 152 to each other in a gas-permeable manner.

The two working spaces 157, 158 and the valve space 159 together form the partially cylindrical hollow space in which the working pistons 151, 152 with the rod 155 and the valve piston 156 are movably disposed. The hollow space is formed by a hollow body made of synthetic material. The hollow space is bounded by walls 160 of the hollow space.

In an otherwise cylindrical outer circumference of the valve piston 156, three circumferential rotation-symmetric grooves 162, 164, 166 are disposed. These grooves 162, 164, 166, together with the wall 160 that surrounds them, form three ring-shaped hollow spaces that are separated from each other. These can be used to switch a valve that is formed with the valve piston 156. In order to form such a valve, five complete openings 168, 170, 172, 174, 176 are disposed in the wall 160 in the area of the valve space 159. The five complete openings 168, 170, 172, 174, 176 are disposed axially (in relation to the cylindrical valve space 159) adjacent to each other. The first central opening 168 opens into a compressed gas port 178. The compressed gas line 180 in the form of a hose can be connected to the compressed gas port 178. The compressed gas line 180 can connect the compressed gas port 178 and thus the first opening 168 to a compressed gas source. The second opening 170 that is disposed axially next to the first opening 168 can be connected to the first working space 157 in a gas-permeable manner via a line 184. The third opening 172 that is disposed axially next to the first opening 168 but opposite the second opening 170 can be connected to the second working space 158 in a gas-permeable manner via a line 182. Thus, in the third differential pressure motor according to the invention that is driven with compressed gas, the connections of the second opening 170 and the third opening 172 to the working spaces 157, 158 are exchanged compared to the first and second exemplary embodiments. The fourth outer opening 174 is connected to the area surrounding the differential pressure motor in a gas-permeable manner. The fifth outer opening 176 is connected to the area surrounding the differential pressure motor in a gas-permeable manner. Therefore, instead of using the differential pressure between a vacuum or underpressure and the ambient air, the differential pressure between the compressed gas 197 and the ambient air is used in the third exemplary embodiment.

The complete openings 168, 170, 172, 174, 176 that lie axially adjacent to each other, together with the wall 160 and the valve piston 156 that is axially movable within the valve space 159 and sealed against the wall 160, and also the grooves 162, 164, 166, form the valve with which the differential pressure motor is controlled. The movement of the valve piston 156 can be initiated by the working pistons 151, 152 that impact the valve piston 156 from both sides and can thus excite an oscillation. The grooves 162, 164, 166 preferably are so broad that in each case, two adjacent openings 168, 170, 172, 174, 176 simultaneously open out into one of the grooves 162, 164, 166. As a result, depending on the position of the valve piston 156, two openings 168, 170, 172, 174, 176 can always be connected to each other in a gas-permeable manner. The grooves 162, 164, 166 are preferably not so broad in the axial direction, however, that three openings 168, 170, 172, 174, 176 can open out into the same groove 162, 164, 166. Further, preferably, the wall 160 between the grooves 162, 164, 166 is sufficiently broad in the axial direction that it at least just covers the second opening 170 and the third opening 172 such that the possibility is excluded that the second opening 170 or the third opening 172 can open out simultaneously into two of the grooves 162, 164, 166 and thus cause a "short circuit" of the differential pressure motor. For this reason, it is also important that the valve piston 156, in particular due to its inertia, automatically travels over the point at which the second opening 170 or the third opening 172 are closed and do not open out into any of the grooves 162, 164, 166. As a result, a dead point position of the differential pressure motor is avoided.

In a first position of the valve piston 156, the first central opening 168 and the adjacent second opening 170 are interconnected in a gas-conductive manner via the central groove 164, and the third opening 172 and the adjacent fourth opening 174 on the edge side are interconnected in a gas-conductive manner via the rear groove 166, and the five openings 168, 170, 172, 174, 176 are otherwise separated from each other in a gas-tight manner by the valve (not the position shown in FIG. 8). In a second position of the valve piston 156 shown in FIG. 8, the first central opening 168 and the third opening 172 are interconnected in a gas-conductive manner via the central groove 164, and the second opening 170 and the adjacent fifth opening 176 on the edge side are interconnected in a gas-conductive manner via the front groove 162, and the five openings 168, 170, 172, 174, 176 are otherwise separated from each other in a gas-tight manner by the valve. The valve piston 156 can be transferred from the first position into the second position by the working pistons 151, 152. When the compressed gas 197 acts on the compressed gas port 178, the first working space 157 is filled with the compressed gas 197 in the first position of the valve piston 156. At the same time, the second working space 158 is connected to the surrounding area in a gas-permeable manner via the third opening 172, the fourth opening 174 and the rear groove 166, so that compressed gas 197 contained in the second working space 158 flows out of the second working space 158 and blows out into the surrounding area. Due to this pressure difference, the first working piston 151 is pushed backward, or the second working piston 152 is pulled backward (to the right in FIG. 8). When the first working piston 151, which is connected to the second working piston 152 via the rod 155, is pulled backward, it impacts the valve piston 156. As a result, the valve piston 156 is thrust out of the first position and transferred into the second position. In this second position of the valve piston 156 (see FIG. 8), the compressed gas 197 can be introduced into the second working space 158, while it is separated from the surrounding area. At the same time, the first working space 157 is connected to the surrounding area in a gas-permeable manner via the second opening 170, the fifth opening 176 and the front groove 162, so that the compressed gas 197 present in the first working space 157 flows out of the first working space 157 and thus, the second working piston 152 is pushed forward or the first working piston 151 is pulled forward (to the left in FIG. 8). As a result, a periodic linear movement or oscillation of the working pistons 151, 152 and the valve piston 156 can be generated. This movement is driven by the first pressure provided by the compressed gas 197 and the surrounding air pressure as the second pressure. Alternatively, the compressed gas port 178 can lie open and a vacuum source or an underpressure source with a pressure lower than the surrounding air pressure can be connected to the fourth opening 174 and the fifth opening 176. The functional principle remains the same. In order to achieve sufficient power of the differential pressure motor, a sufficient differential pressure between the first pressure and the second pressure must be ensured. In addition, an increase in the power of the differential pressure motor can be achieved by enlarging the working surfaces 153, 154.

When the differential pressure motor is at a standstill, the spring (not shown in FIG. 8), which can be disposed as a compression spring between a closure 194 made of synthetic material that bounds the rear side of the second working space 158 and a protruding ring disk (not shown) on the rod 155, can pull back the rod 155 and the working pistons 151, 152. As a result, the valve piston 156 is also automatically brought into a second position. The differential pressure motor is thus prevented from coming to a standstill at a dead point and being unable to re-start.

The working pistons 151, 152 can be connected to the rod 155 via bolts 186. As a result, the assembly of the differential pressure motor is made easier. The rod 155 extends through the two working pistons 151, 152. As a result, the first drive rod 188 protrudes on the front side of the first working piston 151. A second drive rod 190 protrudes on the rear side of the second working piston 152. However, in theory, the second drive rod 190 can be omitted when only a single drive is required. The drive rods 188, 190 can be used to drive tools such as a saw, a rasp, a brush or a pump. For this purpose, one fastening element 192 each can be disposed on the ends of the drive rods 188, 190. The fastening element 192 can take the form of a square hole or a threaded bore, which can be connected to a matching counter-fastening element on a tool.

The first working space 153 is closed on its front side with a closure 193 made of synthetic material, which forms a front surface of the first working space 157. The first drive rod 188 is guided through the closure 193. The closure 193 can be sealed against the first drive rod 188 with a sealing ring, through which the first drive rod 188 slides. The second working space 158 is closed on its front side with the closure 194, which forms a front surface of the second working space 158. The second drive rod 190 is guided through the closure 194. The closure 194 can be sealed against the second drive rod 190 with a sealing ring, through which the second drive rod 190 slides.

The differential pressure motor further has an outer shell 195 made of synthetic material, which encloses the walls 160. The closures 193, 194 can be screwed onto the outer shell 195 with screws 196, wherein one sealing ring can be provided in each case for the purpose of sealing between the closures 193, 194 and the outer shell 195. The openings 168, 170, 172, 174, 176 are sealed against the outer shell 195 with seals. The outer shell 195 can also form the compressed gas port 178 and preferably also be used to form ports for the connection of the second opening 170 with the line 184 to the first working space 157 and for the connection of the third opening 172 with the line 182 to the second working space 158.

In the compressed gas line 180 of the differential pressure motor according to FIG. 8, a manually operable valve element (not shown) can be disposed with which the connection between the compressed gas port 178 and the compressed gas source can be interrupted.

FIGS. 9 to 11 show a second surgical drive system according to the invention with a fourth exemplary differential pressure motor according to the invention, wherein the differential pressure motor according to the fourth exemplary embodiment, in contrast to the differential pressure motor according to the first exemplary embodiment according to FIGS. 1 to 5, has a starting aid in the form of a suitable connection to the vacuum source or underpressure source, which ensures problem-free starting up of the differential pressure motor.

The fourth exemplary differential pressure motor according to the invention has a first working piston 251 and a second working piston 252. The first working piston 251 has a working surface 253 that points in the direction of the front side of the differential pressure motor (on the left in FIGS. 9 to 11). In the same way, the second working piston 252 has a working surface 254 that points in the direction of the rear side of the differential pressure motor (on the right in FIGS. 9 to 11). The work on the two working pistons 251, 252 can thus be performed on respective opposite sides, so that the compressed gas motor can be driven on both sides. The first working piston 251 and the second working piston 252 are firmly connected to each other via a rod 255. The rod 255 keeps the two working pistons 251, 252 at a fixed distance apart from each other. Further, the alignment of the working pistons 251, 252 to each other is fixed by the rod 255.

Between the two working pistons 251, 252, a sheath-shaped valve piston 256 is disposed around the rod 255 and is axially movably supported on the rod 255 (in relation to the rod 255). The valve piston 256 is smaller in its axial extension than the distance between the two working pistons 251, 252 determined by the rod 255. As a result, the valve piston 256 can be moved between the two working pistons 251, 252. According to the invention, the valve piston 256 is smaller than the distance between the two working pistons 251, 252, in relation to the length of the rod 255 between the two working pistons 251, 252 that determines the distance between the two working pistons 251, 252. As a result, an impulse transmission between the sides of the working pistons 251, 252 facing away from the working surfaces 253, 254 onto the valve piston 256 is made possible by a thrust and the mass inertia of the valve piston 256 can be used to push the valve piston 256 beyond a dead point of a valve constructed with the valve piston 256.

The working pistons 251, 252, the rod 255 and the valve piston 256 are located in a hollow space that is partially cylindrical. The first working piston 251 is disposed in a first cylindrical working space 257. The second working piston 252 is disposed in a second cylindrical working space 258. The valve piston 256 is disposed in a cylindrical valve space 259. The first cylindrical working space 257 and the second cylindrical working space 258 have a larger diameter than the valve space 259 disposed between them. The working pistons 251, 252 are movably disposed in the working spaces 257, 258 in the axial direction. The working pistons 251, 252 have a protrusion with a smaller diameter on the side opposite the respective working surface 253, 254, which extends into the valve space 259. As a result, the working pistons 251, 252 can impact onto the valve piston 256 with their protrusions in the valve space 259. In the area of the working surfaces 253, 254, the working pistons 251, 252 have an outer diameter that matches the inner diameter of the respective working space 257, 258. Preferably, the working pistons seal off the respective working space 257, 258 in a gas-tight or pressure-tight manner. For this purpose, circumferential piston rings (see FIGS. 9 to 11) or other seals can be provided on the outer circumference of the working pistons 251, 252.

The valve piston 256 has a cylindrical shape on the outside that matches the cylindrical valve space 259. On the outer circumference on its two ends facing toward the working pistons 251, 252, the valve piston 256 has one circumferential piston ring each (see FIGS. 9 to 11) or another sealing ring. In the interior of the valve piston 256, a gas-permeable passage is disposed that connects the two sides of the valve piston 256 that face toward the working pistons 251, 252 to each other in a gas-permeable manner.

The two working spaces 257, 258 and the valve space 259 together form the partially cylindrical hollow space in which the working pistons 251, 252 with the rod 255 and the valve piston 256 are movably disposed. The hollow space is formed by a hollow body made of synthetic material. The hollow space is bounded by walls 260 of the hollow space.

In an otherwise cylindrical outer circumference of the valve piston 256, three circumferential rotation-symmetric grooves 262, 264, 266 are disposed. These grooves 262, 264, 266, together with the wall 260 that surrounds them, form three ring-shaped hollow spaces that are separated from each other. These can be used to switch a valve that is formed with the valve piston 256. In order to form such a valve, five complete openings 268, 270, 272, 274, 276 are disposed in the wall 260 in the area of the valve space 259. The five complete openings 268, 270, 272, 274, 276 are disposed axially (in relation to the cylindrical valve space 259) adjacent to each other. The first central opening 268 opens into a vacuum port 278. A vacuum line 280 in the form of a hose is connected to the vacuum port 278. The vacuum line 280 can connect the vacuum port 278 and thus the first opening 268 to a vacuum source or underpressure source. The second opening 270 that is disposed axially next to the first opening 268 can be connected to the second working space 258 in a gas-permeable manner via a line 282. The third opening 272 that is disposed axially next to the first opening 268 but opposite the second opening 270 can be connected to the first working space 257 in a gas-permeable manner via a line 284. The fourth outer opening 274 can be connected to the area surrounding the differential pressure motor in a gas-permeable manner. The fifth outer opening 276 can be connected to the area surrounding the differential pressure motor in a gas-permeable manner.

The complete openings 268, 270, 272, 274, 276 that lie axially adjacent to each other, together with the wall 260 and the valve piston 256 that is axially movable within the valve space 259 and sealed against the wall 260, and also the grooves 262, 264, 266, form the valve with which the differential pressure motor is controlled. The movement of the valve piston 256 can be initiated by the working pistons 251, 252 that impact the valve piston 256 from both sides and can thus excite an oscillation. The grooves 262, 264, 266 are preferably so broad that in each case, two adjacent openings 268, 270, 272, 274, 276 simultaneously open out into one of the grooves 262, 264, 266. As a result, depending on the position of the valve piston 256, two openings 268, 270, 272, 274, 276 can always be connected to each other in a gas-permeable manner. The grooves 262, 264, 266 are preferably not so broad in the axial direction, however, that three openings 268, 270, 272, 274, 276 can open out into the same groove 262, 264, 266. Further, preferably, the wall 260 between the grooves 262, 264, 266 is sufficiently broad in the axial direction that it at least just covers the second opening 270 and the third opening 272 such that the possibility is excluded that the second opening 270 or the third opening 272 can open out simultaneously into two of the grooves 262, 264, 266 and thus cause a "short circuit" of the differential pressure motor. For this reason, it is also important that the valve piston 256, in particular due to its inertia, automatically travels over the point at which the second opening 270 or the third opening 272 are closed and do not open out into any of the grooves 262, 264, 266. As a result, a dead point position of the differential pressure motor is avoided.

In a first position of the valve piston 256, the first central opening 268 and the adjacent second opening 270 are interconnected in a gas-conductive manner via the central groove 264, and the third opening 272 and the adjacent fourth opening 274 on the edge side are interconnected in a gas-conductive manner via the rear groove 66, and the five openings 268, 270, 272, 274, 276 are otherwise separated from each other in a gas-tight manner by the valve. This first situation is shown in FIG. 10. In a second position of the valve piston 256 (see FIG. 11), the first central opening 268 and the third opening 272 are interconnected in a gas-conductive manner via the central groove 264, and the second opening 270 and the adjacent fifth opening 274 on the edge side are interconnected in a gas-conductive manner via the front groove 262, and the five openings 268, 270, 272, 274, 276 are otherwise separated from each other in a gas-tight manner by the valve. The valve piston 256 can be transferred from the first position into the second position by the working pistons 251, 252. When the vacuum 47 acts on the vacuum port 278, the second working space 258 is evacuated in the first position of the valve piston 256. At the same time, the first working space 257 is connected to the surrounding area in a gas-permeable manner via the third opening 272, the fourth opening 274 and the rear groove 266, so that air flows into or is present in the first working space 257. Due to this pressure difference, the first working piston 251 is pushed backward, or the second working piston 252 is pulled backward (to the right in FIGS. 9 to 11). When the first working piston 251, which is connected to the second working piston 252 via the rod 255, is pulled back, it impacts the valve piston 256. As a result, the valve piston 256 is thrust out of the first position and transferred into the second position. In this second position of the valve piston 256 (see FIG. 11), the first working space 257 can be evacuated, while it is separated from the surrounding area. At the same time, the second working space 258 is connected to the surrounding area in a gas-permeable manner via the second opening 270, the fifth opening 276 and the front groove 262, so that air flows into the second working space 258 and thus, the second working piston 252 is pushed forward or the first working piston 251 is pulled forward (to the left in FIGS. 9 to 11). As a result, a periodic linear movement or oscillation of the working pistons 251, 252 and the valve piston 256 can be generated. This movement is driven by the vacuum 47 or the underpressure as the first pressure and by the surrounding air pressure as the second pressure. Alternatively, the vacuum port 278 can lie open and a compressed gas source with a pressure higher than the surrounding air pressure can be connected to the fourth opening 274 and the fifth opening 276. The functional principle remains the same. In order to achieve sufficient power of the differential pressure motor, a sufficient differential pressure between the first pressure and the second pressure must be ensured. In addition, an increase in the power of the differential pressure motor can also be achieved by enlarging the working surfaces 253, 254.

The working pistons 251, 252 can be connected to the rod 255 via bolts 286. As a result, the assembly of the differential pressure motor is made easier. The rod 255 extends through the two working pistons 251, 252. As a result, a first drive rod 288 protrudes on the front side of the first working piston 251. A second drive rod 290 protrudes on the rear side of the second working piston 252. However, the second drive rod 290 can also be omitted. The drive rods 288, 290 can be used to drive tools such as a saw, a rasp or a pump (not shown). For this purpose, one fastening element 292 each is disposed on the ends of the drive rods 288, 290. The fastening element 292 can take the form of a square hole or a threaded bore, which can be connected to a matching counter-fastening element on a tool.

The first working space 253 is closed on its front side with a closure 293 made of synthetic material, which forms a front surface of the first working space 257. The first drive rod 288 is guided through the closure 293. The closure 293 is sealed against the first drive rod 288 with a sealing ring, through which the first drive rod 288 slides. The second working space 258 can be closed on its front side with a closure 294, which forms a front surface of the second working space 258. The second drive rod 290 is guided through the closure 294. The closure 294 is sealed against the second drive rod 290 with a sealing ring, through which the second drive rod 290 slides.

The differential pressure motor further has an outer shell 295 made of synthetic material, which encloses the walls 260. The closures 293, 294 can be screwed onto the outer shell 295 with screws 296, wherein for the purpose of sealing between the closures 93, 94 and the outer shell 295, one sealing ring can be provided in each case. The openings 268, 270, 272, 274, 276 are sealed against the outer shell 295 with seals. The outer shell 295 can also form the vacuum port 278 and preferably also be used to form ports for the connection of the second opening 270 with the line 282 to the second working space 258 and for the connection of the third opening 272 with the line 284 to the first working space 257.

In the vacuum line 280 and in the line 284 of the surgical drive system shown in FIGS. 9 to 11, a manually operable valve element 281 is disposed, with which the connection between the vacuum port 278 and the vacuum source or the underpressure source can be interrupted. The valve element 281 has a valve body 297, which is supported in a valve housing 298 in a linearly displaceable manner. A spring 299 in the valve housing 298 presses the valve body 297 into a closed position. A trigger 300 can be used to press the valve body 297 against the spring 299 into the open position, and thus the differential pressure motor can be started up.

The line 284 that connects the third opening 272 to the first working space 257 can therefore also be closed and opened by the valve element 278. In addition, a compensation line 302 is provided that can also be opened and closed with the valve element 281 and which can lead the vacuum 47 or the underpressure into the first working space 257. The compensation line 302 can be connected to the same vacuum source or underpressure source as the vacuum line 280 via a switch 304. On the switch 304, a vacuum port connection piece 306 is disposed to which the vacuum source or the underpressure source can be connected, preferably via a flexible hose (not shown).

The valve element 281 can therefore be a three-way valve element. In an expanded standstill state of the valve element 281 (see FIG. 9), the vacuum line 280 and the line 284 between the first working space 257 and the second opening 272 can be closed by the valve body 297 while the compensation line 302 is open. As a result, the first working piston 251 can be pulled forward when a vacuum 47 is applied to the compensation line 302. In this standstill position, the valve piston 256 is in the first position. When the trigger 300 is operated, the compensation line 302 is closed. At the same time, the line 284 between the first working space 257 and the second opening 272 and the vacuum line 280 can be opened in this way. Since this structure ensures that the valve piston 256 is in the first position when the valve element 281 is operated, a situation is prevented in which the differential pressure motor comes to a standstill at a dead point and cannot re-start. The same starting aid or dead point prevention can also be used in any of the other differential pressure motors shown in FIG. 1 to 5 or 6 and 7 or 8. The starting aid according to the fourth exemplary embodiment does not require a spring.

All parts of the exemplary differential pressure motors and the medical drive system can be made of synthetic material. Thus, the differential pressure motor can be used as a low-cost disposable product for medical applications and can be hygienically combusted following use. As a result, the possibility of contamination of medical staff during disinfection and of patients can be excluded due to the avoidance of multiple use.

As an alternative to the saw 102, other tools such as rasps or brushes (not shown) can be connected with the fastening elements 42, 92, 192, 292, or a liquid pump can be connected and operated with the differential pressure motor, so that with each movement cycle of the rod 5, 55, 155, 255 or of the first drive rod 38, 88, 188, 288 and/or the second drive rod 40, 90, 190, 290, a short spray action with a medical rinsing fluid is generated with the differential pressure motor. In this manner, a lavage system according to the invention can be realized.

The features of the invention disclosed in the above description, as well as in the claims, figures and exemplary embodiments, can be essential, both individually and in any combination, for the realization of the invention in its different embodiments. Although illustrated and described above with reference to certain specific embodiments and examples, the present disclosure is nevertheless not intended to be limited to the details shown. Rather, various modifications may be made in the details within the scope and range of equivalents of the claims and without departing from the spirit of the disclosure.

The invention claimed is:

1. A differential pressure motor comprising:
two working pistons each with a working surface;
a rod that connects the working pistons to each other and keeps them spaced apart from each other;
walls defining a hollow space that is at least partially cylindrical and in which the working pistons and the rod are movably disposed and having five complete openings;
a valve piston movably disposed between and against the working pistons, configured to be driven through thrusts of the working pistons against the valve piston, and movable in the hollow space,
wherein the valve piston with the five complete openings forms a 2/5-way valve with which an alternate impact of a first pressure and a second pressure on the working surfaces of the working pistons is controllable when the first pressure and the second pressure are applied to three of the five complete openings such that a periodic movement of the working pistons and the rod is created in the hollow space, which drives a periodic movement of the valve piston.

2. The differential pressure motor according to claim 1, wherein the working pistons divide the hollow space into at least three areas that are separated from each other.

3. The differential pressure motor according to claim 1, wherein the hollow space has a first working space and a second working space, in which the working pistons are movably disposed, and has a valve space disposed between the working spaces, and wherein the five complete openings are disposed in the valve space in each position of the working pistons.

4. The differential pressure motor according to any claim 1, wherein the valve piston has first and second front surfaces, the working pistons each have a rear side, the hollow space has first and second front surfaces, an axial distance between the first front surface of the valve piston and the rear side of the adjacent working piston is smaller than or equal to the distance between the working surface of this working piston and the first front surface of the hollow space, and an axial distance between the second front surface of the valve piston and the rear side of the adjacent working piston is smaller than or equal to the distance between the working surface of this working piston and the second front surface of the hollow space that is located opposite the first front surface of the hollow space.

5. The differential pressure motor according to claim 1, wherein the working pistons and the rod have a symmetry axis and are disposed to move axially along the symmetry axis in the at least partially cylindrical hollow space.

6. The differential pressure motor according to claim 1, wherein the 2/5-way valve controls an alternate impact of a vacuum or a compressed gas and of the surrounding atmosphere on the working pistons.

7. The differential pressure motor according to claim 1, wherein the working surfaces of the working pistons are aligned facing away from each other.

8. The differential pressure motor according to claim 1, wherein the valve piston is disposed on the rod in an axially displaceable manner.

9. The differential pressure motor according to claim 1, wherein the valve piston is a sheath with three circumferential grooves, which are separated from each other by circumferential bridges, wherein the grooves are at least as broad as the axial distance of two axially adjacent openings of the five openings relative to the sheath, so that with a suitable position of the sheath in the hollow space, two axially adjacent openings open into the same groove of the sheath in the hollow space, and wherein the bridges are as broad, at least in the axial direction, as the two openings of the five openings which are adjacent to the outermost openings.

10. The differential pressure motor according to claim 1, further comprising a vacuum port or a compressed air port and wherein a central opening of the five openings is connected to the vacuum port or the compressed air port and two outer openings of the five openings open outward to an area surrounding the differential pressure motor, or the two outer openings of the five openings are connected to the vacuum port or the compressed air port and the central opening is open outward to the area surrounding the differential pressure motor.

11. The differential pressure motor according to claim 1, wherein one of the two working pistons bounds a first working space, the other of the two working pistons bounds a second working space, an opening of the five openings that is adjacent to an outer opening of the five openings is connected to the first working space in a pressure conductive manner and another opening that is adjacent to an outer opening is connected to the second working space in a pressure conductive manner.

12. The differential pressure motor according to claim 1, further comprising a vacuum port configured to be connected to a vacuum or a compressed gas port configured to be connected to a compressed gas and wherein the valve piston has two sides and wherein when the vacuum is applied to the vacuum port of the differential pressure motor the two working pistons create an oscillating movement of the rod through the periodic change between the effect of the vacuum and the surrounding atmosphere, or
when the compressed gas is fed at the compressed gas port of the differential pressure motor the two working pistons create an oscillating movement of the rod through the periodic change between the effect of the compressed air and the surrounding atmosphere, wherein in both cases, the working pistons periodically impact the valve piston on both sides of the valve piston, thus creating an axial periodic movement of the valve piston, as a result of which the 2/5-way valve is switched.

13. The differential pressure motor according to claim 1, wherein in a first position of the valve piston a first central opening of the five openings and a second opening of the five openings that is adjacent to the first opening are connected in a gas-conductive manner via the 2/5-way valve, and a third opening of the five openings that is located opposite the second opening relative to the first opening and a fourth opening of the five openings adjacent to it are connected to each other in a gas-conductive manner, and the five openings are otherwise separated from each other in a gas-tight manner in the hollow space by the 2/5-way valve, and
in a second position of the valve piston, the first central opening and the third opening are connected to each other in a gas-conductive manner via the 2/5-way valve, and the second opening and a fifth opening of the five openings adjacent to it are connected to each other in a gas-conductive manner, and the five openings are otherwise separated from each other in a gas-tight manner in the hollow space by the 2/5-way valve.

14. The differential pressure motor according to claim 13, wherein the valve piston is transferable from the first position of the valve piston to the second position of the valve piston by an impulse transmission of a first working piston of the two working pistons onto the valve piston, and the valve piston is transferable from the second position of the valve piston to the first position of the valve piston by an impulse transmission of a second working piston of the two working pistons onto the valve piston.

15. The differential pressure motor according to claim 13, wherein the first working piston in the first position of the valve piston is accelerated in the direction of the valve piston due to a pressure bearing on the working surface of the first working piston, and the second working piston in the second position of the valve piston is accelerated in the direction of the valve piston due to a pressure bearing on the working surface of the second working piston.

16. The differential pressure motor according to claim 13, wherein one of the two working pistons bounds a first working space, the other of the two working pistons bounds a second working space, the first working space is connected to the second opening in a gas-conductive manner, and the second working space is connected to the third opening in a gas-conductive manner.

17. The differential pressure motor according to claim 1, further comprising:
a housing that bounds the hollow space and has a front surface with a closed outer side; and
a spring element that is supported on the closed outer side of the front surface of the housing that bounds the hollow space, and which is connected to the rod such that the spring element pulls the rod out of the hollow space to a maximum degree without a force effect from a differential pressure.

18. The differential pressure motor according to claim 1, wherein the two working pistons each have a diameter larger than 10 mm.

19. The differential pressure motor according to claim 1, wherein the two working pistons each have an outer side and the differential pressure motor further comprises:
a housing that bounds the hollow space and has a front side, a rear side, and a guide in the front side and/or the rear side of the housing; and
at least one drive rod disposed on the outer side of at least one of the two working pistons, wherein the at least one drive rod protrudes out from the housing through the front side and/or the rear side of the housing that bounds the hollow space, and the at least one drive rod is movably supported in the guide in the front side and/or the rear side of the housing, wherein the rod which connects the two working pistons is guided through at least one of the working pistons and there forms the at least one drive rod.

20. The differential pressure motor according to claim 19, wherein the at least one drive rod has a front side with a thread configured to engage a counter-thread of a tool that matches the thread, thereby affixing the tool to the at least one drive rod.

21. The differential pressure motor according to claim 1, further comprising a housing that bounds the hollow space and wherein the housing, the two working pistons, the valve piston and the rod are made of a synthetic material.

22. The differential pressure motor according to claim 1, wherein the valve piston has a geometric dimension in the direction of a connecting line between the two working pistons and the geometric dimension is smaller than a distance between the two working pistons.

23. The differential pressure motor according to claim 1, further comprising a starting aid which prevents the differential pressure motor from stopping at a dead point during an interruption of the supply of a working medium from which it is no longer able to start up on its own accord when the working medium is again supplied to the differential pressure motor.

24. A surgical drive system comprising:
a differential pressure motor according to claim 1;
a line that is connected to one of the five openings or to two of the five openings and is configured to be connected to an underpressure source or a compressed gas reservoir or a pump; and
a valve element disposed in the line and configured to interrupt the connection to the underpressure source, the compressed gas reservoir or the pump or to adjust the pressure at the one opening of the five openings or the two openings of the five openings.

25. The surgical drive system according to claim 24, further comprising a handle with a trigger, the handle configured to be held by a user in one hand and the trigger configured to operate the valve element.

26. A medical lavage system for the debridement of soft tissue and/or bone tissue comprising a differential pressure motor according to claim 1 or a surgical drive system according to claim 24, or a medical device for brushing, rasping or sawing soft tissue and/or bone tissue comprising a differential pressure motor according to claim 1 or a surgical drive system according to claim 24.

27. A method for operating the differential pressure motor of claim 1, in which a first working piston and a second working piston are connected via a rod and oscillate linearly in a hollow space, wherein the method comprises the following steps:
A) providing a valve piston, which is disposed in the hollow space between the first working piston and the second working piston in a first position;
B) providing a connection between a vacuum port and a first working space and a connection between a second working space and the surrounding area of the differential pressure motor in the first position of the valve piston, wherein the first working space is bounded by the first working piston and the second working space is bounded by the second working piston;
C) evacuating gas from the first working space and as a result moving the first working piston and the second working piston in the hollow space;
D) impacting the valve piston with the second working piston, so that the valve piston is transferred into a second position;
E) providing a connection between the vacuum port and the second working space and a connection between the first working space and the surrounding area of the differential pressure motor in the second position of the valve piston;
F) evacuating gas from the second working space and flowing in of ambient air into the first working space and as a result, reverse moving of the first working piston and the second working piston in the hollow space; and
G) impacting the valve piston with the first working piston, so that the valve piston is transferred into the first position.

28. The method according to claim 27, wherein the vacuum port or the compressed gas port open out through a first central opening into a valve space in which the valve piston moves, wherein next to the first central opening a second opening is disposed, which connects the valve space to the first working space, next to the first central opening, a third opening is disposed, which connects the valve space to the second working space, next to the second opening, a fourth outer opening is disposed, which connects the valve space to the surrounding area of the differential pressure motor, and next to the third opening, a fifth outer opening is disposed, which connects the valve space to the surrounding area of the differential pressure motor, wherein the step of providing the valve piston includes providing three grooves in the valve piston, so that in the first position of the valve piston, the central first opening is connected to the second opening in a gas-permeable manner, and the third opening is connected to the fifth opening in a gas-permeable manner, and in the second position of the valve piston, the central first opening is connected to the third opening in a gas-permeable manner and the second opening is connected to the fourth opening in a gas-permeable manner, wherein the five openings are otherwise separated from each other by the valve piston.

29. The method according to claim 27, further comprising repeating steps B) to G) after step G) as long as a vacuum or an underpressure is present at the vacuum port or as long as an overpressure is present at the compressed gas port or a compressed gas is introduced.

30. The method according to claim 27, wherein the movement of the first working piston and the second working piston drives a tool or a pump or a lavage system.

31. The method according to claim 27, further comprising switching the differential pressure motor on by opening a valve element in a vacuum line, at the vacuum port or in a compressed gas line at the compressed gas port and switching the differential pressure motor off by closing the valve element.

32. A method for operating the differential pressure motor of claim 1, in which a first working piston and a second working piston are connected via a rod and oscillate linearly in a hollow space, wherein the method comprises the following steps:
A) providing a valve piston, which is disposed in the hollow space between the first working piston and the second working piston in a first position;
B) providing a connection between a compressed gas port and a first working space and a connection between a second working space and the surrounding area of the differential pressure motor in the first position of the valve piston, wherein the first working space is bounded by the first working piston and the second working space is bounded by the second working piston;
C) increasing the gas pressure in the first working space and as a result, moving the first working piston and the second working piston in the hollow space;
D) impacting the valve piston with the first working piston, so that the valve piston is transferred into a second position;
E) providing a connection between the compressed air port and the second working space and a connection between the first working space and the surrounding area of the differential pressure motor in the second position of the valve piston;
F) increasing the gas pressure in the second working space and flowing out of compressed gas from the first working space and as a result, reverse moving of the first working piston and the second working piston in the hollow space; and
G) impacting the valve piston with the second working piston, so that the valve piston is transferred into the first position.

* * * * *